(12) United States Patent
Zannis et al.

(10) Patent No.: US 7,309,606 B2
(45) Date of Patent: Dec. 18, 2007

(54) METHODS AND COMPOSITIONS FOR TREATING HYPERCHOLESTEROLEMIA

(75) Inventors: Vassilis I. Zannis, Newton, MA (US); Kypreos E. Kyriakos, Ialyssos-Rhodes (GR)

(73) Assignees: The Trustees of Boston University, Boston, MA (US); KOS Pharmaceuticals, Inc., Miami, FL (US)

( * ) Notice: Subject to any disclaimer, the term of this patent is extended or adjusted under 35 U.S.C. 154(b) by 0 days.

(21) Appl. No.: 11/220,485

(22) Filed: Sep. 7, 2005

(65) Prior Publication Data

US 2006/0079446 A1 Apr. 13, 2006

Related U.S. Application Data

(60) Provisional application No. 60/607,530, filed on Sep. 7, 2004.

(51) Int. Cl.
C12N 15/00 (2006.01)
C07K 14/00 (2006.01)
C07K 1/00 (2006.01)

(52) U.S. Cl. ..................... 435/440; 530/350; 530/359
(58) Field of Classification Search ............... 530/359, 530/350; 435/440
See application file for complete search history.

(56) References Cited

U.S. PATENT DOCUMENTS 5,811,243 A 9/1998 Strittmatter et al.
5,958,684 A 9/1999 Van Leeuwen et al.
6,290,949 B1 9/2001 French et al.
6,756,523 B1 6/2004 Kahn et al.
2002/0123093 A1* 9/2002 Zannis et al. ............. 435/69.1

FOREIGN PATENT DOCUMENTS

WO WO 96/14837 5/1996

OTHER PUBLICATIONS

Zannis et al. "Mature human apolipoprotein E (apoE) isoprotein, apoE4" alignment result 1, SEQ ID No. 1, Database: A_Geneseq_8, Accession No. AAE13299.*
Cardin et al., "Binding of a High Reactive Heparin to Human Apolipoprotein E: Identification of Two Heparin-Binding Domains," *Biochem. Biophys. Res. Commun.* 134:783-789 (1986).
Chait et al., "Impaired Very Low Density Lipoprotein and Triglyceride Removal in Broad Beta Disease: Comparison With Endogenous Hypertriglyceridemia," *Metabolism* 27:1055-1066 (1978).

(Continued)

*Primary Examiner*—Jon Weber
*Assistant Examiner*—Rita Mitra
(74) *Attorney, Agent, or Firm*—Paul T. Clark; Clark & Elbing LLP

(57) ABSTRACT

The present invention provides methods and compositions for treating hypercholesterolemia using therapeutic apoE proteins. A therapeutic apoE protein is a naturally-occurring apoE protein (e.g., apoE1, apoE2, apoE2*, apoE2**, apoE3, and apoE4) that has one or more amino acid substitutions in the carboxy-terminal region which, when administered to a mammal having hypercholesterolemia, reduces the plasma cholesterol levels without inducing hypertriglyceridemia. The invention also provides a method for reducing plasma cholesterol using low doses of naturally-occurring apoE proteins.

25 Claims, 15 Drawing Sheets

OTHER PUBLICATIONS

Chen et al., "Prolonged Correction of Hyperlipidemia in Mice With Familial Hypercholesterolemia Using an Adeno-Associated Viral Vector Expressing Very-Low Density Lipoprotein Receptor," *Molecular Therapy* 2:256-261 (2000).

Cladaras et al., "The Molecular Basis of a Familial apoE Deficiency. An Acceptor Splice Site Mutation in the Third Intron of the Deficient apoE Gene," *J. Biol. Chem.* 262:2310-2315 (1987).

Cohn et al., "Plasma Concentration of Apolipoprotein E in Intermediate-Sized Remnant-Like Lipoproteins in Normolipidemic and Hyperlipidemic Subjects," *Arterioscler. Thromb. Vas. Biol.* 16:149-159 (1996).

Cullen et al., "Phenotype-Dependent Differences in Apolipoprotein E Metabolism and in Cholesterol Homeostasis in Human Monocyte-Derived Macrophages," *J. Clin. Invest.* 101:1670-1677 (1998).

Dong et al., "Human Apolipoprotein E: Role of Arginine 61 in Mediating the Lipoprotein Preferences of the E3 and E4 Isoforms," *J. Biol. Chem.* 269:22358-22365 (1994).

Dong et al., "Novel Mechanism for Defective Receptor Binding of Apolipoprotein E2 in Type III Hyperlipoproteinemia," *Nature Struc. Biol.* 3:718-722 (1996).

Ehnholm et al., "Role of Apolipoprotein E in the Lipolytic Conversion of β-Very Low Density Lipoproteins to Low Density Lipoproteins in Type III Hyperlipoproteinemia," *Proc. Natl. Acad. Sci. USA* 81:5566-5570 (1984).

Fan et al., "Increased Expression of Apolipoprotein E in Transgenic Rabbits Results in Reduced Levels of Very Low Density Lipoproteins and an Accumulation of Low Density Lipoproteins in Plasma," *J. Clin. Invest.* 101:2151-2164 (1998).

Fazio et al., "Increased Atherosclerosis in Mice Reconstituted With Apolipoprotein E Null Macrophages," *Proc. Natl. Acad. Sci. USA* 94:4647-4652 (1997).

Fazio et al., "Altered Lipoprotein Metabolism in Transgenic Mice Expressing Low Levels of a Human Receptor-Binding-Defective Apolipoprotein E Variant," *J. Lipid Res.* 35:408-416 (1994).

Fazio et al., "Susceptibility to Diet-Induced Atherosclerosis in Transgenic Mice Expressing a Dysfunctional Human Apolipoprotein E (Arg112, Cys142)," *Arterioscler. Thromb.* 14:1873-1879 (1994).

Gerritsen et al., "Hyperlipidemia in APOE2 Transgenic Mice is Ameliorated By a Truncated apoE Variant Lacking the C-Terminal Domain," *J. Lipid Research* 44:408-414 (2003).

Ghiselli et al., "Type III Hyperlipoproteinemia Associated With Apolipoprotein E Deficiency," *Science* 214:1239-1241 (1981).

Herz et al., "Lipoprotein and Receptor Interactions in vivo," *Curr. Opin. Lipidol.* 6:97-103 (1995).

Huang et al., "Effects of Genotype and Diet on Cholesterol Efflux into Plasma and Lipoproteins of Normal, Apolipoprotein A-I-, and Apolipoprotein E-Deficient Mice," *Arterioscler. Thromb. Vasc. Biol.* 17:2010-2019 (1997).

Huang et al., "A Plasma Lipoprotein Containing Only Apolipoprotein E and With γ Mobility on Electrophoresis Releases Cholesterol From Cells," *Proc. Natl. Acad. Sci. USA* 91:1834-1838 (1994).

Huang et al., "Apolipoprotein E2 Reduces the Low Density Lipoprotein Level in Transgenic Mice By Impairing Lipoprotein Lipase-Mediated Lipolysis of Triglyceride-Rich Lipoproteins," *J. Biol. Chem.* 273:17483-17490 (1998).

Huang et al., "Overexpression and Accumulation of Apolipoprotein E as a Cause of Hypertriglyceridemia," *J. Biol. Chem.* 273:26388-26393 (1998).

Huang et al., "Overexpression of Apolipoprotein E3 in Transgenic Rabbits Causes Combined Hyperlipidemia By Stimulating Hepatic VLDL Production and Impairing VLDL Lipolysis," *Arterioscler. Thromb. Vasc. Biol.* 19:2952-2959 (1999).

Innerarity et al., "Enhanced Binding By Cultured Human Fibroblasts of apo-E-Containing Lipoproteins As Compared With Low Density Lipoproteins," *Biochemistry* 17:1440-1447 (1978).

Innerarity et al., "The Receptor-Binding Domain of Human Apolipoprotein E: Binding of Apolipoprotein E Fragments," *J. Biol. Chem.* 258:12341-12347 (1983).

Ji et al., "Intravenous Heparinase Inhibits Remnant Lipoprotein Clearance From the Plasma and Uptake By the Liver:in vivo Role of Heparan Sulfate Proteoglycans," *J. Lipid Res.* 36:583-592 (1995).

Ji et al.,"Role of Heparan Sulfate Proteoglycans in the Binding and Uptake of Apolipoprotein E-Enriched Remnant Lipoproteins By Cultured Cells," *J. Biol. Chem.* 268:10160-10167 (1993).

Ji et al., "Secretion-Capture Role for Apolipoprotein E in Remnant Lipoprotein Metabolism Involving Cell Surface Heparan Sulfate Proteoglycans," *J. Biol. Chem.* 269:2764-2772 (1994).

Ji et al., "Variable Heparan Sulfate Proteoglycan Binding of Apolipoprotein E Variants May Modulate the Expression of Type III Hyperlipoproteinemia," *J. Biol. Chem.* 269:13421-13428 (1994).

Jong et al., "Nascent Very-Low-Density Lipoprotein Triacylglycerol Hydrolysis By Lipoprotein Lipase is Inhibited By Apolipoprotein E In a Dose-Dependent Manner," *Biochem. J.* 328:745-750 (1997).

Kim D. et al., "Human Apolipoprotein E Receptor 2: A Novel Lipoprotein Receptor of the Low Density Lipoprotein Receptor Family Predominantly Expressed in Brain," *J. Biol. Chem.* 271:8373-8380 (1996).

Kuipers et al., "Impaired Secretion of Very Low Density Lipoprotein-Triglycerides By Apolipoprotein E-Deficient Mouse Hepatocytes," *J. Clin. Invest.* 100:2915-2922 (1997).

Kypreos et al., "Domains of Apolipoprotein E Contributing to Triglyceride and Cholesterol Homeostasis in Vivo," *J. Biol. Chem.* 276:19778-19786 (2001).

Linton et al., "Prevention of Atherosclerosis in Apolipoprotein E-Deficient Mice by Bone Marrow Transplantation," *Science* 267:1034-1037 (1995).

Luo et al., "Structure and Expression of Dog Apolipoprotein A-1, E, and C-1 mRNAs: Implications for the Evolution and Functional Constraints of Apolipoprotein Structure," *J. Lipid Res.* 30:1735-1746 (1989).

Mahley et al., "Apolipoprotein E: From Atherosclerosis to Alzheimer's Disease and Beyond," *Curr. Opin. Lipidol.* 10:207-217 (1999).

Mahley et al., "Interaction of Plasma Lipoproteins Containing Apolipoproteins B and E With Heparin and Cell Surface Receptors," *Biochim. Biophys Acta* 575:81-91 (1979).

Mann et al., "Apolipoprotein E-1 $_{\text{Harrisburg}}$: A New Variant of Apolipoprotein E Dominantly Associated With Type III Hyperlipoproteinemia," *Biochim. Biophys. Acta* 1005:239-244 (1989).

Matsushima et al., "Primary Structure of Guinea Pig Apolipoprotein E," *Nucleic Acids Research* 18:202 (1989).

Oka et al., "Long-Term Stable Correction of Low-Density Lipoprotein Receptor-Deficient Mice With a Helper-Dependent Adenoviral Vector Expressing the Very Low-Density Lipoprotein Receptor," *Circulation* 103:1274-1281 (2001).

Rall et al., "Structrual Basis for Receptor Binding Heterogeneity of Apolipoprotein E From Type III Hyperlipoproteinemic Subjects," *Proc. Natl. Acad. Sci., USA* 79:4696-4700 (1982).

Rall et al., "Type III Hyperlipoproteinemia Associated With Apolipoprotein E Phenotype E3/3: Structure and Genetics of an Apolipoprotein E3 Variant," *J. Clin. Invest.* 83:1095-1101 (1989).

Reddick et al., "Atherosclerosis in Mice Lacking apo E: Evaluation of Lesional Development and Progression," *Arterioscler. Thromb.* 14:141-147 (1994).

Rensen et al., "Apolipoprotein E Effectively Inhibits Lipoprotein Lipase-Mediated Lipolysis of Chylomicron-Like Triglyceride-Rich Lipid Emulsions in vitro and in vivo," *J. Biol. Chem.* 271:14791-14799 (1996).

Rudinger, "Characteristics of the Amino Acids as Components of A Peptide Hormone Sequence," *Peptide Hormones*, Parson ed., p. 1-7 (1976).

Schaefer et al., "Familial Apolipoprotein E Deficiency," *J. Clin. Invest.* 78:1206-1219 (1986).

Shimano et al., "Inhibition of Diet-Induced Atheroma Formation in Transgenic Mice Expressing Apolipoprotein E in the Arterial Wall," *J. Clin. Invest.* 95:469-476 (1995).

Smit et al., "Genetic Heterogeneity in Familial Dysbetalipoproteinemia. The E2 (lys 146→gln) Variant Results in a Dominant Mode of Inheritance," *J. Lipid Res.* 31:45-53 (1990).

Takahashi et al., "Rabbit Very Low Density Lipoprotein Receptor: A Low Density Lipoprotein Receptor-Like Protein With Distinct Ligand Specificity," *Proc. Natl. Acad. Sci. USA* 89:9252-9256 (1992).

Tsukamoto et al., "Liver-directed Gene Transfer and Prolonged Expression of Three Major Human ApoE Isoforms in ApoE-deficient Mice," *J. Clin. Invest.* 100(1):107-114 (1997).

van Vlijmen et al., "In the Absence of Endogenous Mouse Apolipoprotein E, Apolipoprotein E*2(Arg-158→Cys) Transgenic Mice Develop More Severe Hyperlipoproteinemia Than Apolipoprotein E*3-Leiden Transgenic Mice," *J. Biol. Chem.* 271:30595-30602 (1996).

van den Maagdenberg et al., "Apolipoprotein E*3-Leiden Allele Results From a Partial Gene Duplication in Exon 4," *Biochem. Biophys. Res. Commun.* 165:851-857 (1989).

van den Maagdenberg et al., "Transgenic Mice Carrying the Apolipoprotein E3-Leiden Gene Exhibit Hyperlipoproteinemia," *J. Biol. Chem.* 268:10540-10545 (1993).

van Dijk et al., "In LDL Receptor Deficient Mice, Catabolism of Remnant Lipoproteins Requires a High Level of apoE But is Inhibited By Excess apoE," *J. Lipid. Res.* 40:336-344 (1999).

Verma et al., "Gene Therapy—Promises, Problems and Prospects," *Nature* 389:239-242 (1997).

Wardell et al., "Apolipoprotein E2-Christchurch (136 Arg→Ser). New Variant of Human Apolipoprotein E in a Patient With Type III Hyperlipoproteinemia," *J. Clin. Invest.* 80:483-490 (1987).

Wardell et al., "Apolipoprotein E3-Leiden Contains a Seven-Amino Acid Insertion That is a Tandem Repeat of Residues 121-127," *J. Biol. Chem.* 264:21205-21210 (1989).

Weisgraber et al., "Human Apolipoprotein E: Determination of the Heparin Binding Sites of the Apolipoprotein E3," *J. Biol. Chem.*, 261:2068-2076 (1986).

Weisgraber et al., "The Receptor-Binding Domain of Human Apolipoprotein E: Monoclonal Antibody Inhibition of Binding" *J. Biol. Chem.* 258:12348-12354 (1983).

Westerlund et al., "Discrete Carboxyl-Terminal Segments of Apolipoprotein E Mediate Lipoprotein Association and Protein Oligomerization," *J. Biol. Chem.* 268:15745-15750 (1993).

Wilson et al., "Salt Bridge Relay Triggers Defective LDL Receptor Binding By a Mutant Apolipoprotein," *Structure* 2:713-718 (1994).

Wilson et al., "Three-Dimensional Structure of the LDL Receptor-Binding Domain of Human Apolipoprotein E," *Science* 252:1817-1822 (1991).

Wolf et al., "Characterization and Immunohistochemical Localization of $\alpha_2$-Macroglobulin Receptor (Low Density Lipoprotein Receptor-Related Protein) in Human Brain," *Am. J. Pathol.* 141:37-42 (1992).

Breslow et al., "Identification and DNA Sequence of a Human Apolipoprotein E cDNA Clone," *J. Biol. Chem.* 257:14639-14641, 1982.

Wetterau et al., "Human Apolipoprotein E3 in Aqueous Solution," *J. Biol. Chem.* 263: 6240-6248, 1988.

\* cited by examiner 1 of 2

2 of 2

METHODS AND COMPOSITIONS FOR TREATING HYPERCHOLESTEROLEMIA

CROSS REFERENCE TO RELATED APPLICATIONS

This application claims priority from U.S. Provisional Application Ser. No. 60/607,530, filed on Sep. 7, 2004, which is hereby incorporated by reference in its entirety.

STATEMENT AS TO FEDERALLY FUNDED RESEARCH

This invention was funded by grant HL68216 from the National Institute of Health. The government may have certain rights in the invention.

BACKGROUND OF THE INVENTION

ApoE is a polymorphic protein in humans and promotes the clearance of lipoproteins remnants. There are three common alleles ($\epsilon 4$, $\epsilon 3$, and $\epsilon 2$) that encode apoE in humans. The three isoforms (apoE4, apoE3, and apoE2, respectively) result from mutations at amino acid residues 112 and 158. ApoE4 contains arginine at both positions. ApoE3 contains cysteine at residue 112 and arginine at reside 158. ApoE2 contains cysteine at both positions. There also exists three rare alleles: apoE1 (G127D/R158C); apoE2* (R145C); and apoE2** (K146Q).

ApoE is a component of VLDL, IDL, HDL, chylomicrons and chylomicron remnants, and is required for the clearance of lipoprotein remnants from the circulation. Lipoprotein-bound apoE is the ligand for the LDL receptor as well as other LDL receptor family members and SR-BI. In vitro and in vivo studies have shown that the apoE2 isoform and other apoE mutants that prevent binding of apoE-containing lipoproteins to the LDL receptor are associated with high plasma cholesterol levels and cause premature atherosclerosis in humans and experimental animals. ApoE promotes cholesterol efflux and thus may contribute to cell and tissue cholesterol homeostasis and protection from atherosclerosis. ApoE is also a risk factor for Alzheimer's disease and may contribute to lipid homeostasis in the brain.

It was shown that overexpression of full-length apoE (by infection of mice with $1\text{-}2\times 10^9$ pfu) did not correct the high cholesterol levels of the apoE$^{-/-}$ mice; in contrast, it increased VLDL triglyceride secretion and induced hypertriglyceridemia. Overexpression of apoE3 or apoE4 also aggravated the hypercholesterolemia in apoE2 knock-in mice. The high cholesterol profile of apoE$^{-/-}$ mice or the apoE2 knock-in mice was corrected by infection with truncated apoE forms lacking different segments of the C-terminal domain. The hypertriglyceridemia induced by full-length apoE was independent of the apoE phenotype and mouse strain and could be corrected by overexpression of lipoprotein lipase. In normal C57BL/6 mice overexpression of full-length apoE induced combined hyperlipidemia, characterized by high cholesterol and high triglyceride levels.

Previous in vitro experiments have shown that residues 260-269 of apoE are important for binding of apoE to lipids and lipoproteins. Use of a series of apoE deletion mutants extending from amino acid 1 to amino acids 185, 202, 229 or 259 mapped the region responsible for the hypertriglyceridemia between amino acids 260-299 of apoE. Deletion of residues 260-299 of apoE diminished greatly the ability of the truncated apoE to solubilize multilamellar dimyristoyl-L-$\alpha$-phosphatidyl-choline (DMPC) vesicles. Further, deletion of residues 166-299, 203-299, or 230-299 completely eliminates the ability of apoE to solubilize multilamellar DMPC vesicles. Thus, the carboxy-terminal 260-299 amino acids of apoE is involved in the initial association of apoE with phospholipid, a process that may be required for the formation of apoE-containing lipoproteins. Once apoE is lipoprotein-bound, it may be taken up by the LDL receptor. The contribution of receptors other than the LDL receptor in the clearance of apoE-containing lipoprotein remnants was previously assessed by studies in apoE$^{-/-}\times$LDLr$^{-/-}$ double-deficient mice (Kypreos, et al., 2003). However, neither the full-length apoE2 or apoE4 nor the truncated apoE2-202 (deletion of residues 203-299) or apoE4-202 corrected the high cholesterol profiles of the apoE$^{-/-}\times$LDLr$^{-/-}$ double-deficient mice. Thus, in the absence of this receptor, lipoprotein receptor related protein (LRP) and heparan sulfate proteoglycans are not sufficient to clear the lipoproteins remnants, which accumulate in the plasma of the double-deficient mice (Kypreos, et al., 2003).

SUMMARY OF THE INVENTION

The present invention is based on the discovery that the cholesterol-lowering effect of naturally-occurring apoE proteins can be substantially dissociated from the hypertriglyceridemic effect by selective mutation of amino acids in the C-terminal region of the protein. These mutated apoE proteins ("therapeutic apoE proteins"), and the nucleic acids that encode them, may be used therapeutically for treating hypercholesterolemia and associated disorders such as atherosclerosis.

The invention features therapeutic apoE proteins, and nucleic acids encoding therapeutic apoE proteins, which are substantially identical to naturally-occurring apoE protein (e.g., apoE4 (SEQ ID NO. 1), apoE3 (SEQ ID NO. 2), apoE2 (SEQ ID NO. 3), apoE1 (SEQ ID NO. 4), apoE2* (SEQ ID NO. 5), and apoE2** (SEQ ID NO. 6)) but contain at least one amino acid substitution or deletion in the carboxy-terminal region. Preferably, the apoE protein is a human apoE protein. Preferably, the substitution or deletion is in helix 8 or helix 9 of the apoE protein. Particularly useful helix 8 substitutions include L261X, W264X, F265X, L268X, and V269X, wherein X is any amino acid. Preferably, X is alanine. Thus, in preferred embodiments, the therapeutic apoE protein contains at least one of L261A, W264A, F265A, L268A, or V269A. More preferably, the therapeutic apoE protein contains two, three, four, or all five of the amino acid substitutions L261A, W264A, F265A, L268A, and V269A. Therefore, particularly useful therapeutic apoE proteins having helix 8 substitutions include, for example, apoE2[L261A/W264A/F265A/L268A/V269A], apoE3[L261A/W264A/F265A/L268A/V269A], apoE4[L261A/W264A/F265A/L268A/V269A].

Particularly useful helix 9 substitutions include W276X, L279X, V283X, V287X, and V293X, wherein X is any amino acid. Preferably, X is alanine. Thus, in preferred embodiments, the therapeutic apoE protein contains at least one of W276A, L279A, V283A, V287A, and V293A. More preferably, the therapeutic apoE protein contains the amino acid substitutions W276A, L279A, V283A, V287A, and V293A. Therefore, particularly useful therapeutic apoE proteins having helix 9 substitutions include, for example, apoE2[W276A/L279A/V283A/V287A/V293A], apoE3[W276A/L279A/V283A/V287A/V293A], and apoE4[W276A/L279A/V283A/V287A/V293A].

The therapeutic proteins of the invention can be used to reduce plasma cholesterol in a mammal (e.g., a human), without inducing hypertriglyceridemia. Any of the therapeutic apoE proteins of the previously described embodiments may be used in this method. The therapeutic apoE protein may be administered by any appropriate route; however, intravenous injection is preferred. Any condition that is characterized by hypercholesterolemia may be treated according to the methods of this invention including, for example, atherosclerosis.

The therapeutic proteins of the invention can also be used to reduce plasma cholesterol in a mammal (e.g., a human), without inducing hypertriglyceridemia, by administering to the mammal an effective amount of a nucleic acid encoding a therapeutic apoE protein, operably linked to a promoter that, when expressed in the target cells, is capable of expressing said therapeutic apoE protein which is a naturally-occurring apoE protein having at least one amino acid substitution in the carboxy-terminal region. Preferably, the therapeutic apoE nucleic acids are contained within a recombinant viral vector such as an adeno-associated vector, a lentiviral vector, a herpes viral vector, or a retroviral vector. Preferably, the vectors are administered to the liver or are administered by intravenous injection. The vectors may be associated with liposomes to facilitate delivery.

The therapeutic proteins of the invention can also used to treat hypercholesterolemia in a mammal (e.g., a human) by administering to the mammal a naturally-occurring apoE protein (e.g., apoE1, apoE2, apoE2*, apoE2**, apoE3, or apoE4) in an amount sufficient to reduce plasma cholesterol without inducing hypertriglyceridemia. Preferably, the method results in a steady-state plasma apoE concentration of less than 60 mg/dl.

By "therapeutic apoE proteins" is meant any protein which is substantially identical to a naturally-occurring apoE protein and which contains amino acid substitutions and/or deletions in the carboxy-terminal region which, when administered to a mammal, reduce plasma cholesterol levels without inducing hypertriglyceridemia.

By "carboxy-terminal region," when referring to any apoE protein, is meant the region corresponding to amino acid residues 260-299 of human apoE.

By "reducing plasma cholesterol," following a therapeutic intervention, is meant any reduction in plasma cholesterol of at least 5%, 10%, 15%, 20%, 25%, 30%, 40%, 50% or more relative to the plasma cholesterol levels prior to therapy. Preferably, plasma cholesterol is reduced to a level that is typical of age and gender matched peers.

By "without inducing hypertriglyceridemia," following a therapeutic intervention, is meant the inducing no more than a 25%, 50%, 75%, or 100% increase in plasma triglyceride levels relative to pre-treatment levels.

By "substantially identical" is meant a polypeptide or nucleic acid exhibiting at least 75%, but preferably 85%, more preferably 90%, most preferably 95%, or even 99% identity to a reference amino acid or nucleic acid sequence. For polypeptides, the length of comparison sequences will generally be at least 20 amino acids, preferably at least 30 amino acids, more preferably at least 40 amino acids, and most preferably 50 amino acids. For nucleic acids, the length of comparison sequences will generally be at least 60 nucleotides, preferably at least 90 nucleotides, and more preferably at least 120 nucleotides.

By "operably linked" is meant that a nucleic acid molecule and one or more regulatory sequences (e.g., a promoter) are connected in such a way as to permit expression and/or secretion of the product (i.e., a polypeptide) of the nucleic acid molecule when the appropriate molecules (e.g., transcriptional activator proteins) are bound to the regulatory sequences.

By "an effective amount" is meant an amount of a compound, alone or in a combination according to the invention, required to inhibit the growth of a neoplasm in vivo. The effective amount of active compound(s) used to practice the present invention for therapeutic treatment of hypercholesterolemia varies depending upon the manner of administration, the age, body weight, and general health of the subject. Ultimately, the attending physician or veterinarian will decide the appropriate amount and dosage regimen. Such amount is referred to as an "effective" amount.

DETAILED DESCRIPTION

Figure 10:
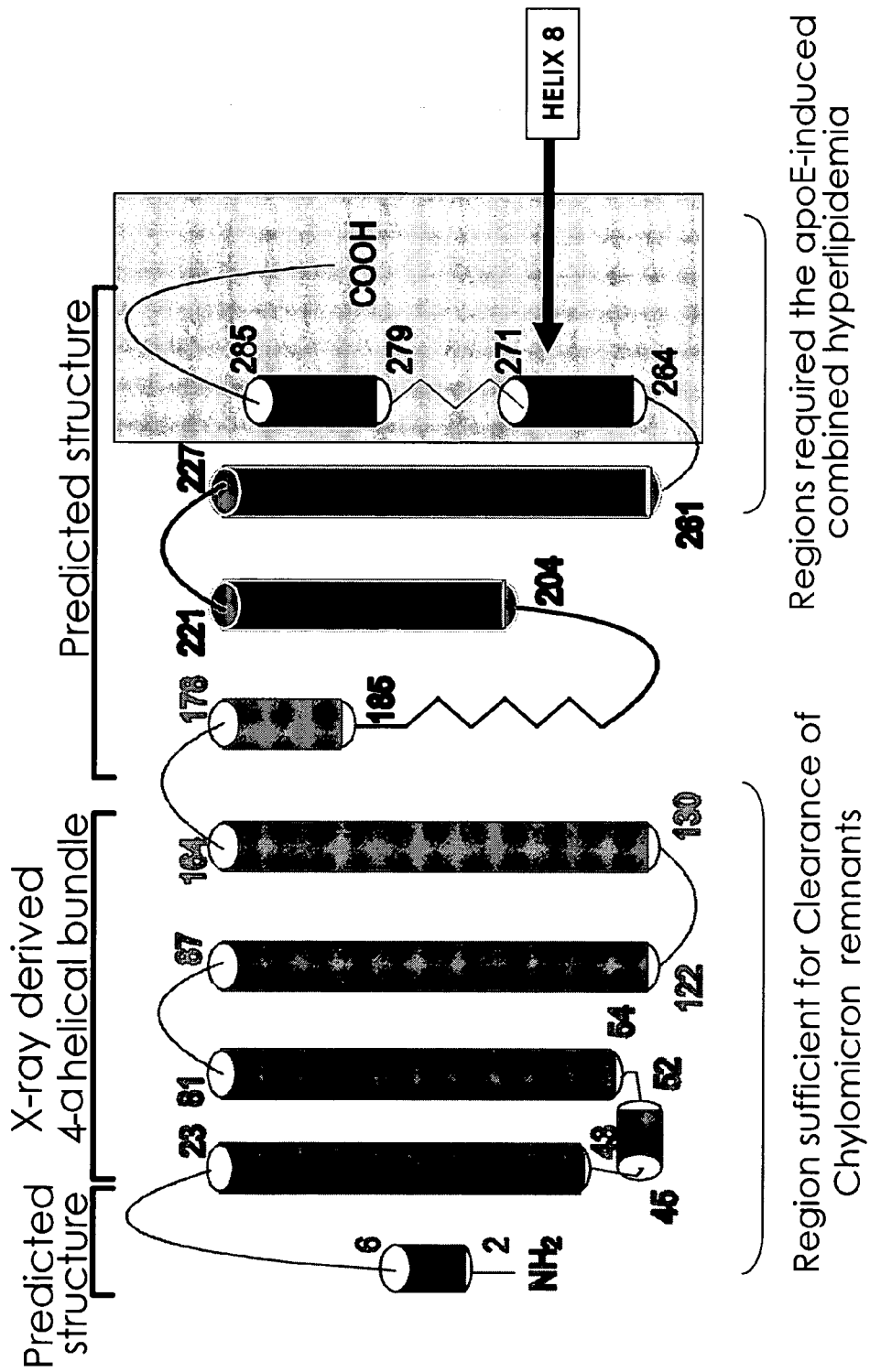
FIG. 10 is a schematic diagram of the predicted structure of wild-type ApoE.

The present invention is based on the finding that particular hydrophobic residues of helix 8 of apoE are critical for proper VLDL processing and the formation of spherical HDL (see FIG. 10). These results demonstrate that, with appropriate modification, the cholesterol-lowering effect of apoE may be dissociated from its hypertriglyceridemic effect.

The present invention maps the residues in the carboxy-terminal region of apoE which are responsible for hypertriglyceridemia. Two regions of apoE between residues 260 to 299 contain hydrophobic amino acids that are required for the association of apoE with lipid and lipoproteins. The first region includes amino acids L261, W264, F265, L268 and V269, and the second region includes amino acids W276, L279, V280, V283. A BLAST search of NCBI database shows that both regions are highly conserved among mammalian species. As described in more detail below, in vivo adenovirus-mediated gene transfer of the two apoE mutants established unequivocally that the hydrophobic residues of apoE between amino acids 261 to 269 accounts for most of the induction of hypertriglyceridemia by affecting the secretion of VLDL triglycerides. Virtually all of the remaining hypertriglyceridemic effect is associated with the hydrophobic amino acids in the 276 to 283 region.

In Vitro Production of ApoE-mut1 and ApoE-mut2 in HTB-13 Cells

Construction of Recombinant Adenoviruses Expressing the Wild-Type and the Mutant Forms of Forms apoE4.

Two apoE4 mutants were generated using the mutagenesis kit QuickChange-XL (Stratagene). The mutants are:
apoE4-mut1: apoE4[W276A/L279A/V280A/V283A], and
apoE4-mut2: apoE4[L261A/W264A/F265A/L268A/V269A]

The mutagenic primers used are apoE4mut1-s (5'-gcctt ccagg cccgc gccaa gagcg cggcc gagcc cgcgg cggaa gacat gcagc gc-3'), apoE4-mut1-a (5'-gcgct gcatg tcttc cgccg cgggc tcggc cgcgc tcttg gcgcg ggcct ggaa ggc-3'), apoE4-mut2-s (5'-gacat gcagc gccag gcggc cgggg cggcg gaga ggcgc aggct gccgt-3') and apoE4-mut2-a (5'-gccca cggca gcctg cgcct tctcc gccgc cccgg ccgcc tggcg ctgca-3'). In both mutagenic reactions, the vector pGEM7-apoE4 containing Exons II, III, and IV of the human apoE was used as a template. Following 18 cycles of PCR amplification of the template DNA, the PCR product was treated with DpnI to digest plasmids containing methylated DNA in one or both of their strands. The reaction product consisting of plasmids containing newly synthesized DNA carrying the mutations of interest were used to transform XL-10 blue competent bacteria cells (Stratagene). Ampicillin-resistant clones were selected, and plasmid DNA was isolated from these clones, and subjected to sequencing to confirm the presence of the point mutations.

The recombinant adenoviruses were constructed as previously described (Kypreos, et al., *J. Biol. Chem.* 276: 19778-19786, 2001) using the Ad-Easy-1 system where the adenovirus construct is generated in bacteria BJ-5183 cells. Correct clones were propagated in RecA DH5a cells. The recombinant adenoviral vectors were linearized with PacI and used to infect 911 cells. Following large-scale infection of HEK 293 cell cultures, the recombinant adenoviruses were purified by two consecutive CsCl ultracentrifugation steps, dialyzed and titrated. Usually, titers of approximately $5 \times 10^{10}$ pfu/ml were obtained.

Quantification of Human apoE

Human apoE4 concentrations were measured using sandwich ELISA. Affinity purified polyclonal goat anti-human apoE antibodies were used for coating 96-well Maxosorb immunoplates (NUNC), and the same polyclonal goat anti-human apoE linked to horseradish peroxidase was used as the secondary antibody. The immunoperoxidase procedure was employed for the colorimetric detection of apoE by measuring the change in the absorption at 450 nm, using tetramethylbenzidine as substrate. Pooled plasma from healthy human subjects with known apoE level was used as a standard.

Cell Culture Studies

Figure 1:
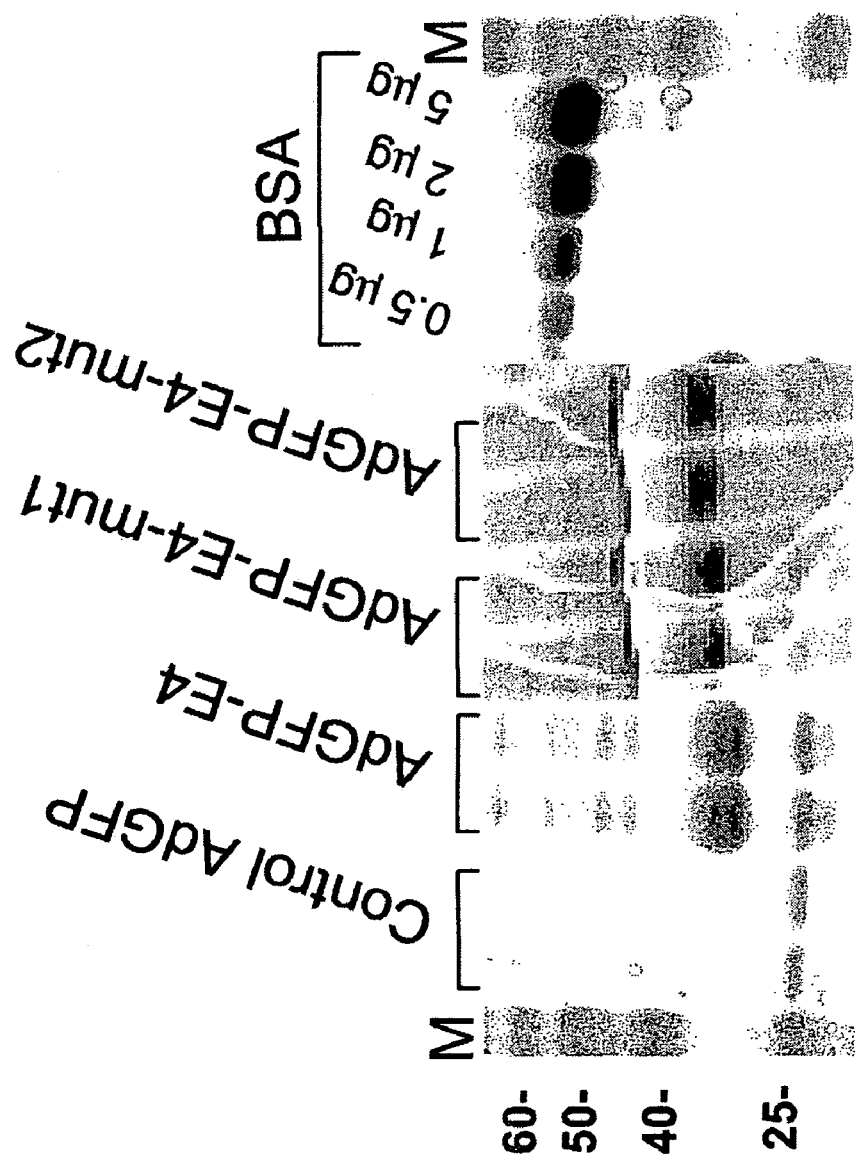
FIG. 1 is an SDS-PAGE gel of culture medium of HTB-13 cells infected with control adenoviruses and adenoviruses expressing WT apoE4, apoE4-mut1, and apoE4-mut2. M indicates molecular weight markers (New England Biolabs). ApoE levels may be assessed by comparison with the intensity of the bands of samples containing 0.5-2.5 mg of bovine serum albumin (BSA).

Human HTB 13 cells (SW1783, human astrocytoma) grown to confluence in medium containing 10% fetal calf serum (FCS), were infected with AdGFP-E4 or the adenoviruses expressing the mutant apoE forms AdGFP-E4-mut1 and AdGFP-mut2 at a multiplicity of infection (m.o.i.) of 20. Twenty-four hours post-infection, cell were washed twice with Phosphate buffered saline (PBS), and preincubated in serum free medium for two hours. Following an additional wash with PBS, fresh serum free medium was added. After 24 h of incubation, medium was collected and analyzed by sandwich enzyme linked immunoabsorbent assay (ELISA) and SDS-PAGE for apoE expression. The ELISA results (FIG. 1) showed that apoE4, apoE4-mut1 and apoE4-mut2 are secreted efficiently at comparable levels (in the range of 130 and 170 mg of apoE per ml respectively, 24 h post infection).

Residues L261, W264, F265, L268, V269 are Responsible for Hypertriglyceridemia

Figure 2:
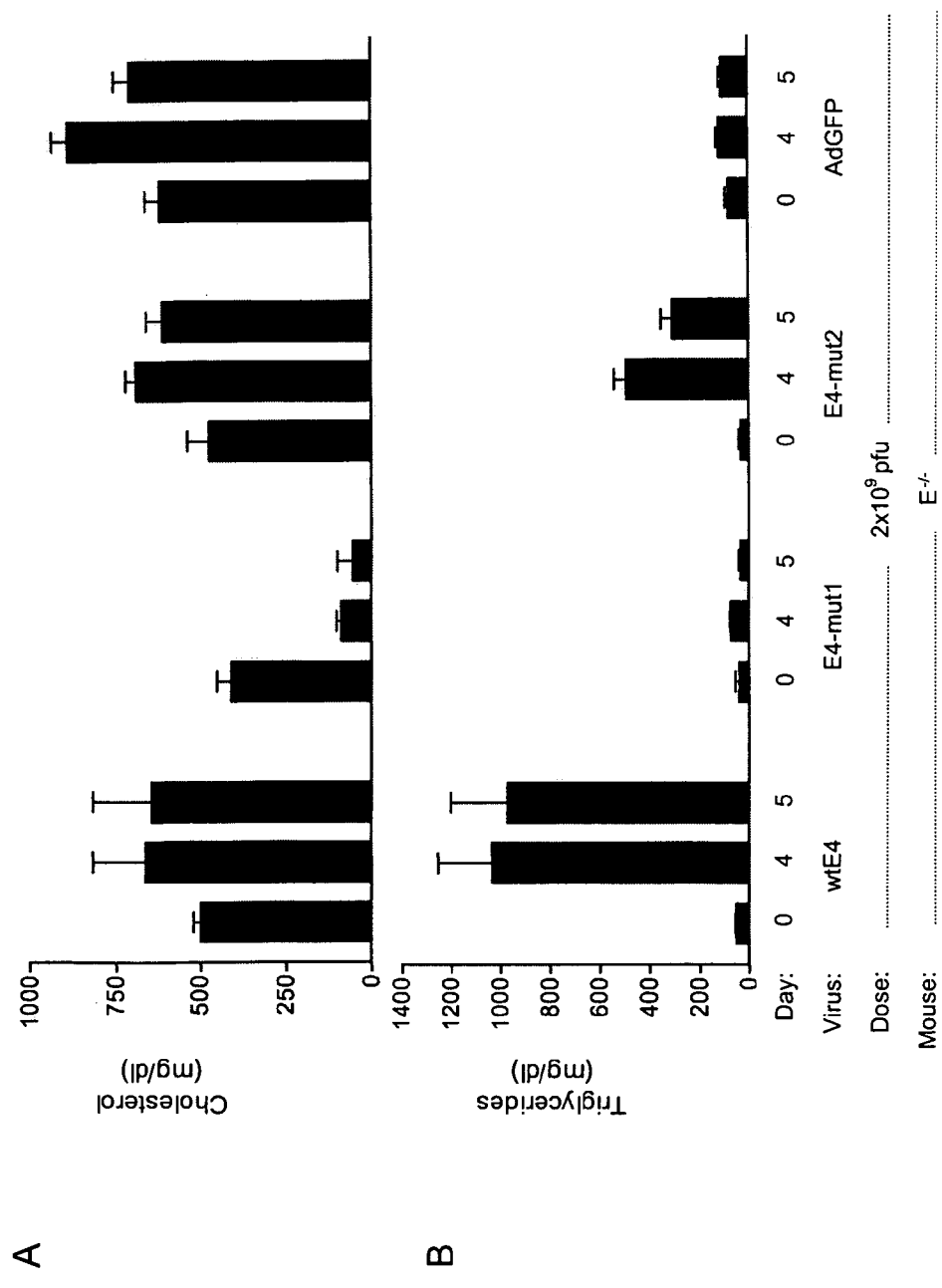
FIGS. 2A and 2B are bar graphs showing the time course of changes in plasma cholesterol (FIG. 2A) and triglyceride (FIG. 2B) levels of apoE$^{-/-}$ mice infected with a control adenovirus (AdGFP) or recombinant adenoviruses expressing wild-type apoE4, apoE4-mut1, or apoE4-mut2. Mice were infected in triplicate with $2\times10^9$ pfu of adenovirus.

We used adenovirus mediated gene transfer in apoE$^{-/-}$ mice to assess the effects of the wild-type apoE4 and the two mutants, apoE4-mut1 or apoE4-mut2 forms on the induction of hyperlipidemia in vivo. The apoE$^{-/-}$ mice were infected with either the control adenovirus AdGFP, the recombinant adenoviruses expressing the wild type apoE4, apoE4-mut1, or apoE4-mut2, and analyzed 4 to 8 days post-infection. Lipid analysis showed that the infection of mice with $2 \times 10^9$ pfu of recombinant adenovirus expressing the apoE4 or apoE4-mut2 did not cause a significant reduction in the plasma cholesterol levels 4 or 5 days post-infection and induced severe hypertriglyceridemia, as compared to the mice infected with the control virus and non-infected mice (FIG. 2A,B). In contrast, infection of mice with recombinant adenovirus expressing apoE4-mut1, at a dose of $2 \times 10^9$, normalized plasma cholesterol levels 4 or 5 days post-infection and did not cause hypertriglyceridemia (FIG. 2A,B).

Figure 3:
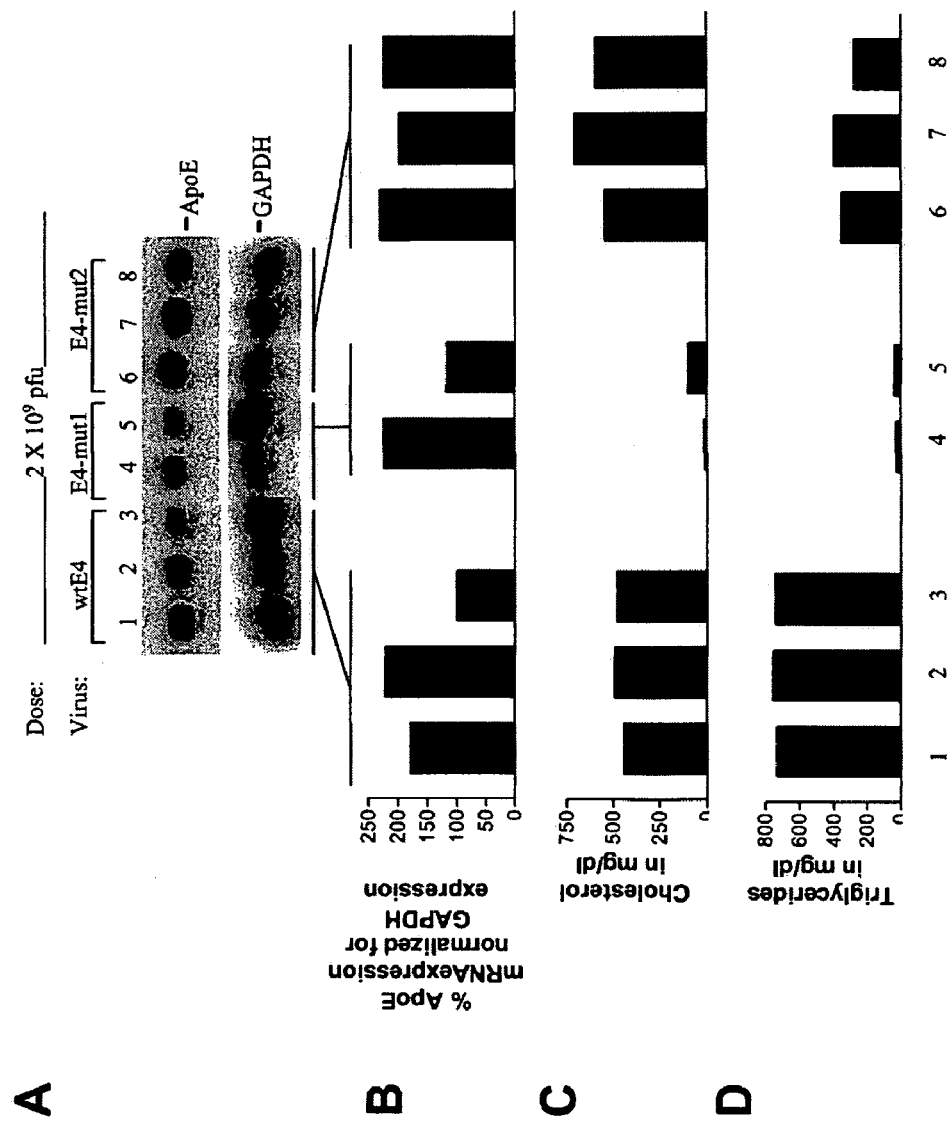
FIG. 3A is an autoradiogram of a Northern blot of total RNA preparation from livers of infected mice five days after infection and analyzed for the expression of apoE and GAPDH mRNA.
FIG. 3B is a bar graph quantifying the apoE mRNA levels normalized for GAPDH mRNA levels. Quantification was done by phosphorimager using the ImageQuant program (version 4.2A).
FIG. 3C is a bar graph showing the cholesterol levels of the individual mice.
FIG. 3D is a bar graph showing the triglyceride levels of the individual mice.

To assess the expression of apoE4, apoE4-mut1, and apoE4-mut2 in infected mice, at least 3 infected mice from each group were sacrificed 5 days post-infection. Total RNA was isolated from the livers of these mice and analyzed for apoE mRNA expression by Northern blotting and quantitated by phosphorimaging. The apoE mRNA levels in mice infected with a dose of $2 \times 10^9$ pfu AdGFP-E4 are similar to those in mice infected with $2 \times 10^9$ pfu AdGFP-E4-mut1 or AdGFP-E4-mut2 (FIG. 3A,B). These findings are in agreement with cell culture data, where we see similar levels of apoE4 and apoE4-mut1 and apoE4-mut2 protein expression following adenovirus infection. However, only apoE4-mut1 clears efficiently the cholesterol of apoE-deficient mice without causing hypertriglyceridemia; whereas, the full-length apoE4 and the apoE4-mut2 did not correct the levels of the apoE$^{-/-}$ mice and induced hypertriglyceridemia. Thus, the different effects of apoE4 and apoE4-mut1 or apoE4-mut2 on hypertriglyceridemia most likely are not due to different levels of expression and secretion of the full-length and the mutant apoE forms. The hypertriglyceridemia observed in the apoE4-mut2 was less severe than that of the WT apoE4. (FIG. 3C,D). Therefore, the hydrophobic residues L261, W264, F265, L268, V269 in helix 8 of the human apoE are mainly responsible for the apoE-induced hypertriglyceridemia, whereas residues Tyr276Ala, Leu279Ala, Val280Ala, Val282Ala located in helix 9 have a relatively smaller effect on the induction of hypertriglyceridemia.

Animal Studies, RNA and Protein Analyses

Female apoE-deficient mice 4-6 week old were used in these studies. Groups of 8-10 female mice were injected intravenously through the tail-vein with doses ranging from $5 \times 10^8$ to $1 \times 10^{10}$ pfu. Blood was obtained from the tail vein after a 4 h fast preceding adenoviral injection and 0, 3, 4, and 5 days after injection. Aliquots of plasma were stored at 40 and $-20°$ C. Three or more animals from each group was sacrificed on each of the indicated days and the mRNA levels in the mouse liver were analyzed by Northern blotting, and quantitated by phosphorimaging as described (Kypreos et al., 2001).

Triglyceride-Rich VLDL Particles Accumulate with ApoE4 and ApoE4-mut2 Overexpression, but are Cleared by ApoE4-mut1

Figure 4:
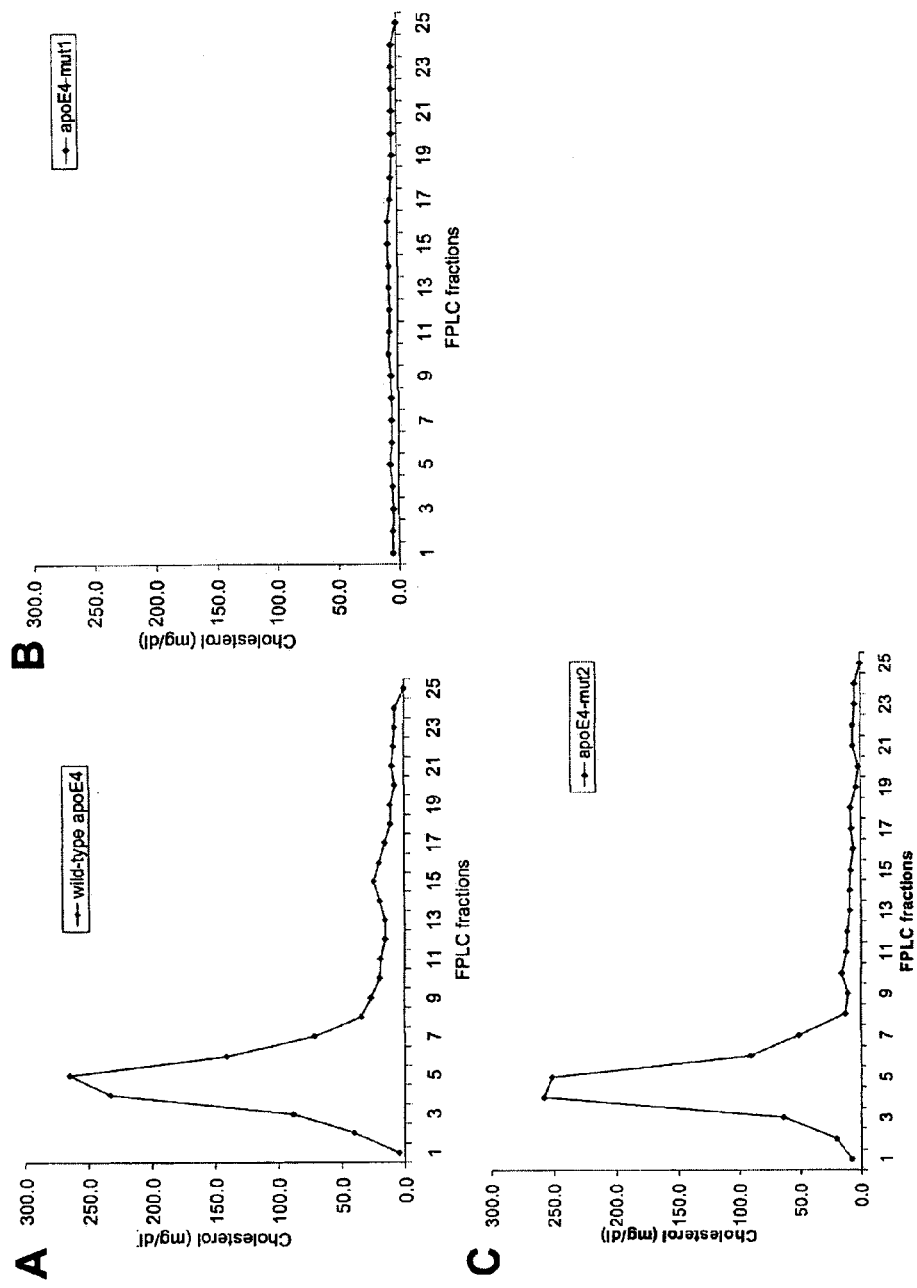
FIG. 4A-F are graphs showing the FPLC profiles of serum cholesterol (FIGS. 3A-C) and triglycerides (FIGS. 3D-F) of adenovirus-infected mice. Serum samples obtained from uninfected apoE-deficient mice, or mice infected with $2\times^9$ pfu of the recombinant adenoviruses expressing wild-type apoE4 (FIGS. 3A and 3D) or AdGFP-apoE4-mut2 (FIGS. 3B and 3E) or apoE4-mut1 (FIGS. 3C & 3F) five days post-infection.
Figure 4:
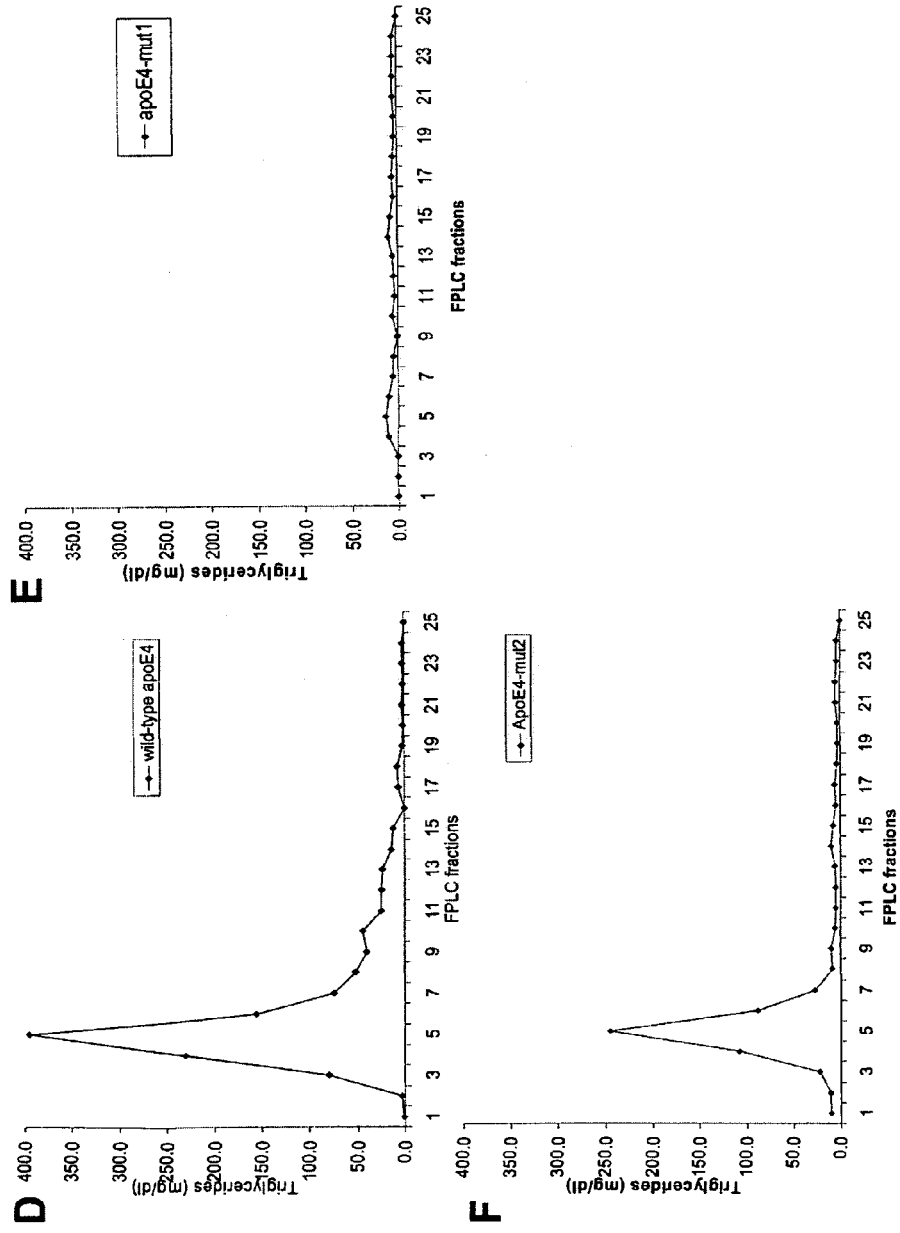

FPLC analysis of plasma from adenovirus-infected mice showed that in mice expressing apoE4 or apoE4-mut1 five days post-infection, cholesterol and triglyceride levels were high and were distributed predominantly in the VLDL region (FIG. 4A,C,D,F). In contrast, in mice infected with AdGFP-E4-mut1, cholesterol and triglycerides were low and were distributed in all lipoprotein fractions five days post-infection (FIG. 4B,E). As an additional control, infection of mice with $2 \times 10^9$ pfu of the control virus AdGFP, did not result in any change in the cholesterol and triglyceride profiles of the apoE$^{-/-}$ mice.

Figure 5:
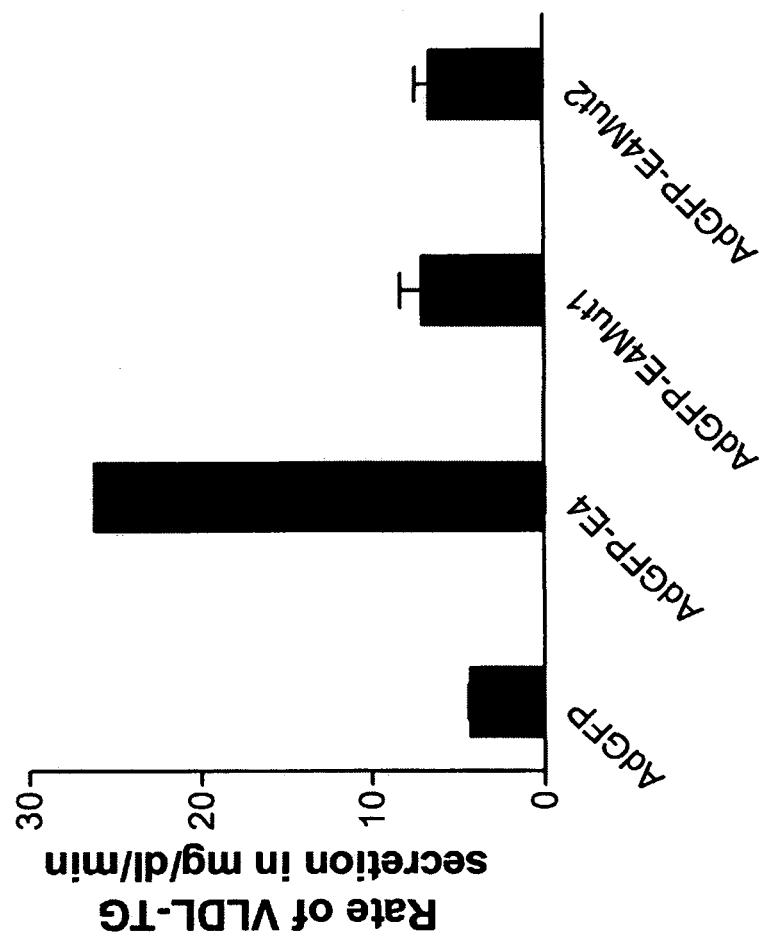
FIG. 5 is a bar graph showing the hepatic VLDL-triglyceride production of mice infected with either the control AdGFP adenovirus or recombinant adenoviruses expressing wild-type apoE4, apoE4-mut1, or apoE4mut2. Triton WR1339 (500 mg/kg body weight) was injected into 3 fasted mice per virus group. Serum samples were collected at 20, 40, and 60 min after the injection with the detergent. Control serum samples were isolated 1 minute after the injection with the detergent. Serum triglyceride levels were determined and a linear graph of serum triglyceride concentration vs. time were generated. The rate of VLDL-triglyceride secretion expressed in mg/dl/min was calculated from the slope of the linear graph for each individual mouse. The mean±standard deviation of the individual rates of VLDL-triglyceride production per virus group are presented in the form of bar graphs.

ApoE4-mut1 and apoE4-mut2 have a minor effect on the rate of hepatic VLDL triglyceride secretion. The rate of hepatic VLDL triglyceride secretion in the plasma was determined following injection of Triton WR1339 five days after the infection with the recombinant adenoviruses. The rate of triglyceride secretion increased 5.5-fold in mice infected with adenoviruses expressing WT apoE4 as compared to mice infected with AdGFP control and adenoviruses expressing either apoEmut1 or apoE4mut2 in mice infected with adenoviruses. The rate of VLDL triglyceride secretion increased 1.9-fold, as compared to mice infected with the control adenoviruses (FIG. 5). Thus, residues L261, W264, F265, L268, V269 in helix 8, or residues W276, L279, V280 and V283 in helix 9 of the human apoE have a major effect on the secretion of hepatic triglycerides and when they are altered to the less hydrophobic Ala, the rate of triglyceride secretion is diminished.

FPLC Analysis and Lipid Determination

For FPLC analysis of serum samples, 12 ml of serum were diluted 1:5 with PBS, and loaded onto a Superose 6 column in a SMART micro FPLC system (Pharmacia), and eluted with PBS. A total of 25 fractions of 50 ml volume each were collected for further analysis. Triglycerides and cholesterol where determined using the GPO-Trinder Kit (Sigma) and CHOL-MPR3 kit (Boehringer-Mannheim), according the manufacturers instructions. The triglyceride and cholesterol concentrations of the serum and the FPLC fractions were determined spectrophotometrically at 540 nm and 492 nm, respectively, as previously described (Kypreos et al., 2001).

Rate of VLDL Triglyceride Production in C57/BL6 Mice Infected with Different apoE Forms.

VLDL triglyceride secretion was determined following infection of C57/BL6 mice with $2 \times 10^9$ pfu of adenoviruses expressing either WT apoE4, apoE4mut1, or the control AdGFP viruses. Four days post-infection, mice were fasted for 4 h and then injected with Triton-WR1339 at a dose of 500 mg/kg of body weight, using a 15% solution (w/v) in 0.9% NaCl. Triton-WR 1339 has been shown to completely inhibit VLDL catabolism. Serum samples were isolated 20, 40, 60 and 90 minutes after injection with Triton WR 1339. Serum triglycerides were measured and the rate of VLDL-triglyceride secretion expressed in mg/dl/min was determined as previously described (Kypreos et al., 2001). The mean±standard deviation of three to four experiments are presented in the form of a bar graph.

Figure 6:
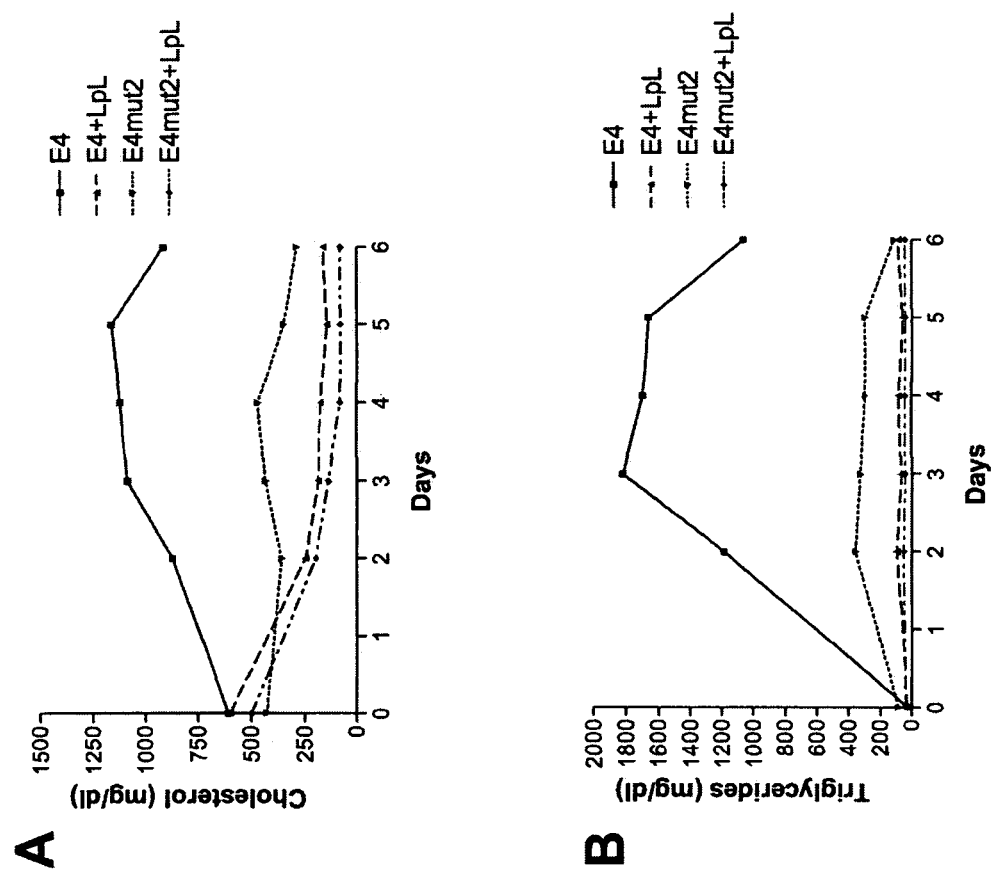
FIGS. 6A and 6B are graphs showing the time course of cholesterol (FIG. 6A) and triglyceride (FIG. 6B) levels of apoE$^{-/-}$ mice infected with a recombinant adenovirus expressing either wild-type apoE4 or apoE4-mut2 alone or either in conjunction with human lipoprotein lipase (LpL).
Figure 7:
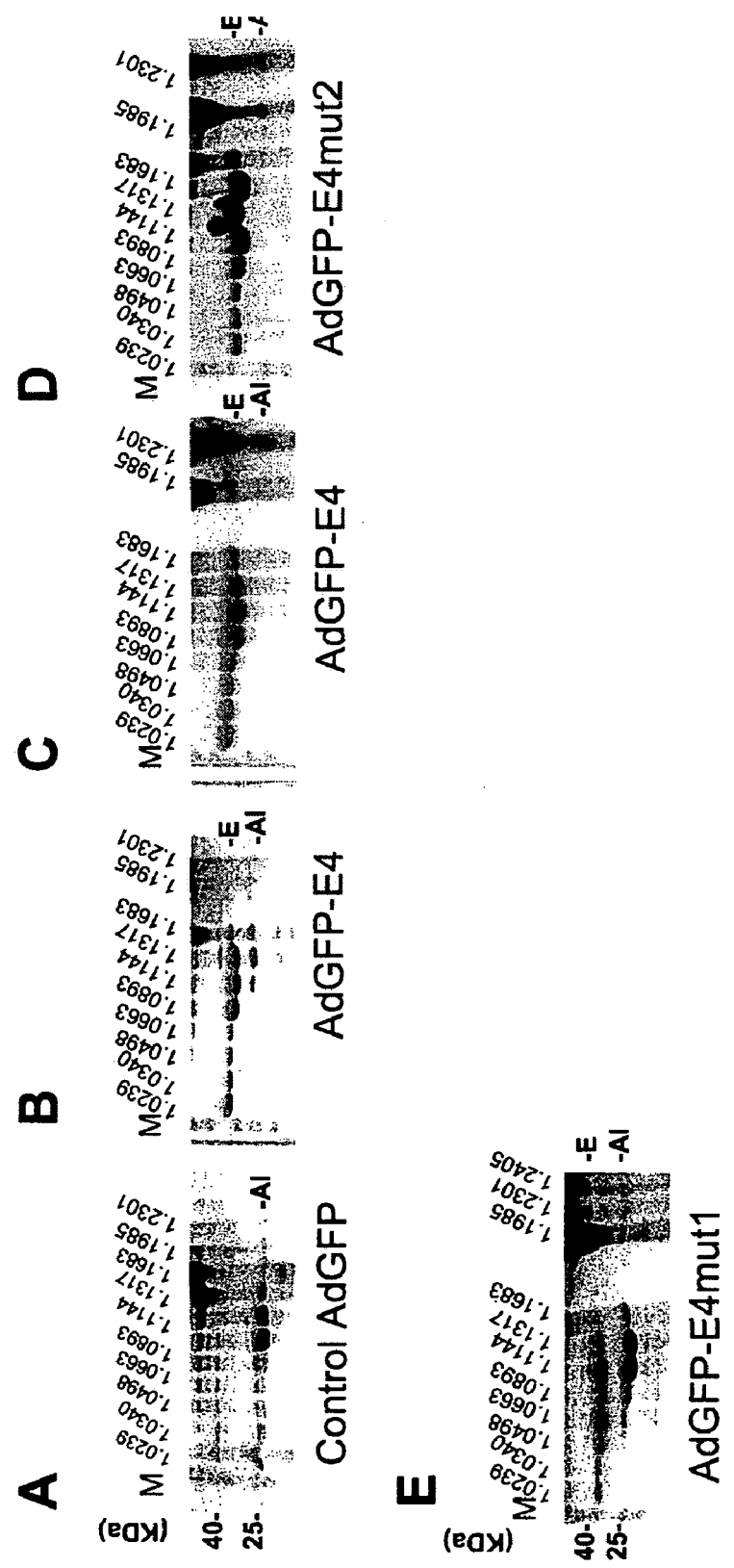
FIGS. 7A-E are SDS-PAGE gels showing the distribution of apoE in different lipoprotein fractions following density gradient ultracentrifugation. Plasma samples were obtained from apoE$^{-/-}$ mice expressing wild-type apoE4 (FIGS. 7B and 7C), apoE4-mut1 (FIG. 7E), apoE4-mut2 (FIG. 7D), and mice infected with control adenoviruses (FIG. 7A). The samples were fractionated by density gradient ultracentrifugation prior to SDS-PAGE analysis.
Figure 8:
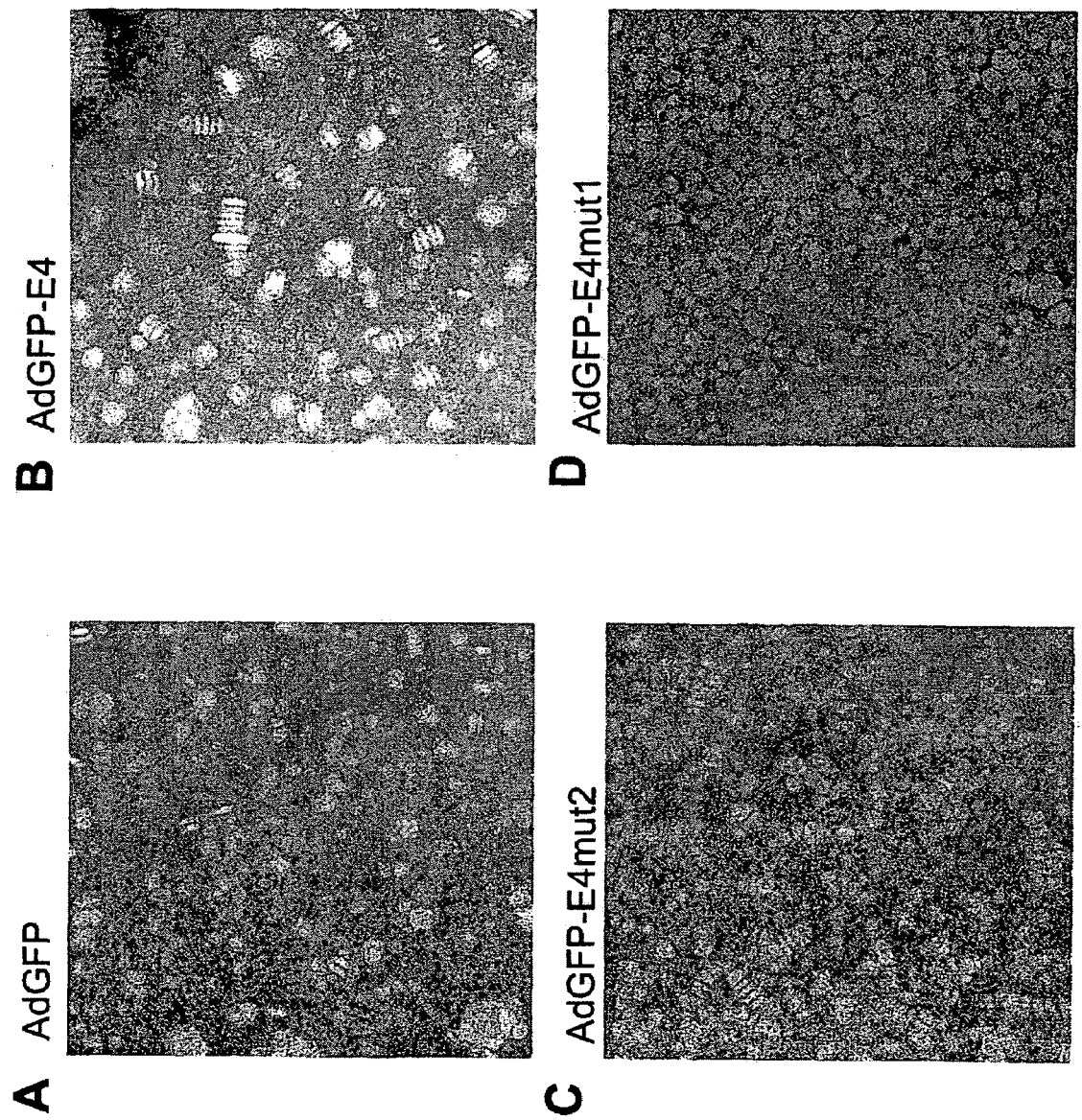
FIGS. 8A-D are electron micrographs of HDL fractions obtained from the plasma of mice infected with control adenovirus (FIG. 8A) or adenoviruses expressing wildtype apoE4 (FIG. 8B), apoE4-mut1 (FIG. 8D), or apoE4-mut2 (FIG. 8C).

Co-Expression of ApoE4 or ApoE4-mut2 with Lipoprotein Lipase Normalizes Lipid Levels in ApoE$^{-/-}$ Mice To test potential insufficiency in the activity of lipoprotein lipase in the induction of hypertriglyceridemia apoE$^{-/-}$ mice were coinfected with $2 \times 10^9$ pfu of the adenovirus-expressing E4 or apoE4-mut1 and $1 \times 10^9$ pfu of adenovirus-expressing human lipoprotein lipase. This treatment corrected both the hypertriglyceridemia and the hyper-cholesterolemia that occurs in mice treated with apoE4 or apoE4-mut2 alone (FIG. 6). The endogenous lipoprotein lipase activity is rate-limiting for the lipolysis and clearance of VLDL under conditions of apoE overexpression.

Figure 9:
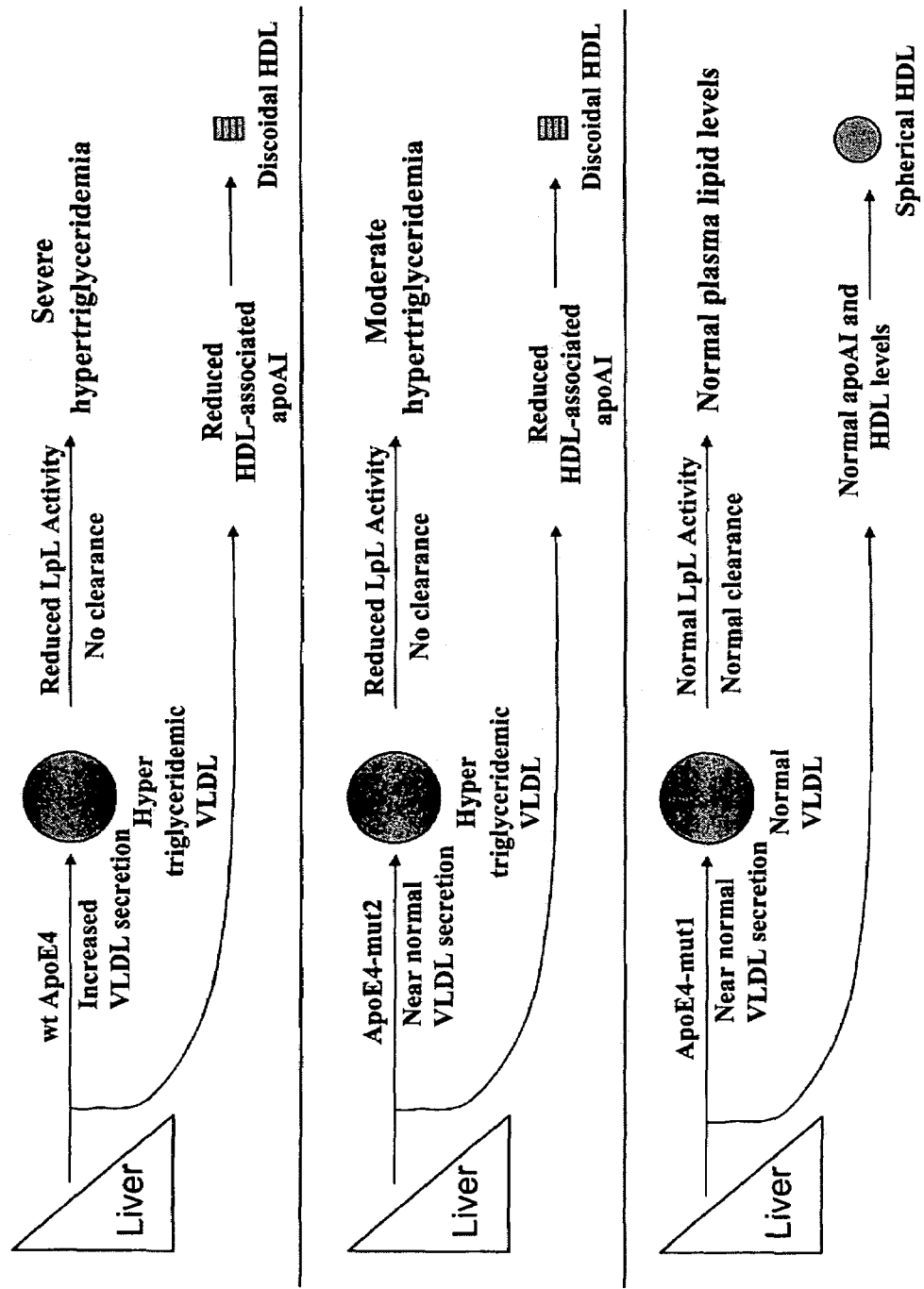
FIG. 9 is a series of schematic representations showing the effect of biosynthesis and catabolism of VLDL and HDL in apoE$^{-/-}$ mice overexpressing wildtype apoE4 (top), apoE4-mut2 (middle), or apoE4-mut1 (bottom).

Increased levels of the plasma lipoprotein lipase, by coinfection with recombinant adenoviruses expressing the human lipoprotein lipase, corrected the apoE-induced dyslipidemia in apoE$^{-/-}$ mice that overexpress full-length apoE. Thus, under conditions of apoE overexpression the activity of lipoprotein lipase becomes rate-limiting for the clearance of the hypertriglyceridemic VLDL (FIG. 9). Substantial but less severe hypertriglyceridemia is also observed by overexpression of apoE4-mut2, which is also corrected by coinfection with the lipoprotein lipase-expressing adenovirus. The difference in the severity of the hypertriglyceridemia between WT apoE4 and apoE4mut2 may be related to the increased VLDL triglyceride secretion caused by the WT apoE4 (FIG. 9).

ApoE4 and ApoE4-mut2, but not ApoE4mut1, Displace ApoA-I from the HDL Region and Promotes Formation of Discoidal HDL Particles To establish the ability of apoE4, apoE4-mut1 and apoE4-mut2 to associate with different lipoproteins, 300 ml of serum from mice infected either recombinant adenoviruses expressing apoE4, or apoE4-mut1 or apoE4-mut2 were fractionated by density gradient ultracentrifugation. Fractions of different densities were isolated and analyzed by SDS-PAGE followed either by staining with Coomassie brilliant blue stain or by western blotting using anti-apoE antibodies. It was found that both the full-length apoE4, and the apoE4-mut1 and apoE4-mut2 mutants, associate with lipoproteins that float in the HDL region and to a lesser extent with particles in the LDL and IDL regions. Overexpression of both wt apoE4 and apoE4-mut2 resulted in displacement of apoA-I from HDL, whereas overexpression of apoE4-mut1 does not displace apoA-I from the HDL density region (FIG. 7A-E). ApoA-I levels of mice infected with the apoE4-mut1 appear to be similar to those of apoE$^{-/-}$ mice, and over 90% of apoA-I was found in the HDL following density gradient ultracentrifugation.

In contrast, in mice infected with either WT apoE4 or the apoE4mut2, the apoA-I that was associated with HDL was greatly reduced. EM analysis of the fraction 6 to 8 containing apoA-I showed that overexpression of WT apoE4 or apoE4mut2 was associated with the formation of discoidal HDL particles, whereas expression of apoE4-mut2 at similar levels were associated with the formation of spherical HDL particles (FIG. 8A-D).

The differences in the biogenesis and catabolism of VLDL and HDL in apoE$^{-/-}$ mice that overexpress apoE4 and apoE4mut2 are summarized in FIG. 9A-C. In summary, apoE4 and apoE4-mut2 displaced apoA-I from HDL and promoted the formation of discoidal HDL. In contrast, apoE-mut1 did not displace apoA-I from the HDL region, and did not affect the formation of spherical HDL particles (FIG. 9). The findings demonstrate that wild-type apoE4 is less desirable for controlling cholesterol levels because they negatively impact the formation or the stability of HDL. This undesirable property of WT apoE to reduce plasma HDL levels can be overcome in the recombinant apoE4-mut1 or similar molecules. The ability of recombinant apoE forms such as apoE4-mut1 which promote cholesterol clearance without induction of hypertriglyceridemia are useful therapeutic agents to correct remnant removal disorders and control hypercholesterolemia.

Electron Microscopy

Aliquots of the fractions from equilibrium density gradient centrifugation after dialysis against ammonium acetate and carbonate buffer were stained with sodium phosphotungstate, visualized in the Phillips CM-120 electron microscopy (Phillips Electron Optics, Eindhoven, Netherlands), and photographed as described previously (Kypreos et al., 2001). The photomicrographs were taken at ×75,000 magnification and enlarged three times.

Density Gradient Ultracentrifugation

To assess the ability of WT and mutant apoE forms to associate with different lipoproteins, 0.3 ml of culture medium was brought to a volume of 0.5 ml with PBS and adjusted to density 1.23 g/ml with KBr. This solution was then overlaid with 1 ml of 1.21 g/ml KBr, 2.5 ml of 1.063 g/ml KBr, 0.5 of 1.019 g/ml KBr and 0.5 ml of saline. The mixtures were centrifuged for 22 h in a SW-41 rotor at 30,000 rpm. Following ultracentrifugation, 10 fractions of 0.5 ml were collected and analyzed by SDS-PAGE.

Low Steady-State Plasma ApoE Levels Clear Plasma Cholesterol in ApoE$^{-/-}$ Mice It has been established that high levels of plasma apoE are associated with high triglyceride levels in humans and in experimental animal models. To identify the steady-state apoE concentrations that can induce hypertriglyceridemia, apoE$^{-/-}$ mice were infected with either a low ($5 \times 10^8$ pfu) or a high ($2 \times 10^9$ pfu) dose of a recombinant adenovirus expressing the wild-type apoE4. Plasma samples collected from day 1 to day 8 post-infection were analyzed for cholesterol, triglyceride and apoE levels.

Figure 11:
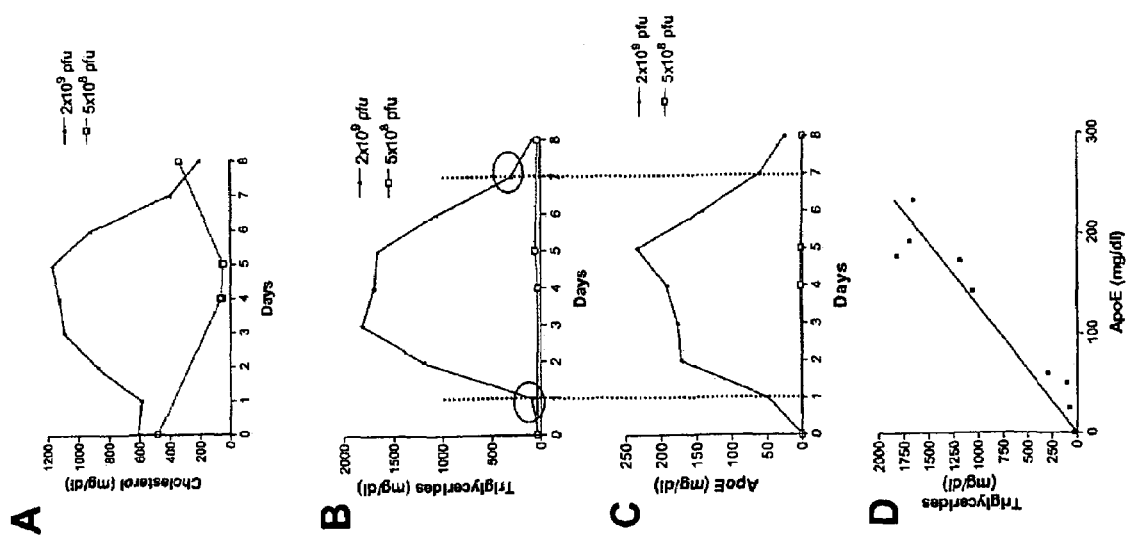
FIGS. 11A-C are graphs of the time course of plasma cholesterol, triglyceride, and apoE levels, respectively, in apoE$^{-/-}$ mice infected with low ($5 \times 10^8$ pfu) and high ($2 \times 10^9$ pfu) doses of recombinant adenovirus expressing apoE4.
FIG. 11D is a graph of the correlation between plasma apoE levels triglyceride levels in apoE$^{-/-}$ mice.

In mice infected with $5 \times 10^8$ pfu of the apoE4-expressing adenovirus, cholesterol levels were normalized on days 4 and 5 post-infection without induction of hypertriglyceridemia, while the steady-state plasma levels of human apoE4 were in the range of 3-5 mg/dl (FIG. 11A-C). This demonstrates that low levels of apoE production by the liver suffices for the clearance of lipoprotein remnants.

High doses ($2 \times 10^9$ pfu) of apoE aggravated the hypercholesterolemia and induced severe hypertriglyceridemia. The severity of the hypertriglyceridemia showed a linear correlation with plasma apoE levels (FIG. 11D). Hypertriglyceridemia was observed at steady-state plasma aopE concentration of approximately 60 mg/dl; whereas, slightly elevated triglyceride levels were observed at apoE concentration fo 50 mg/dl (compare FIGS. 11B and 11C).

Construction of Recombinant Adenovirus Expressing Wild-Type Human ApoE4

The construction of the recombinant adenovirus expressing the wild-type human apoE4 form has been described previously (Kypreos, et al., 2003). Recombinant adenoviruses were generated in bacteria BJ-5183 cells and were used to infect 911 cells (He, et al., *Proc. Natl. Acad. Sci. USA*, 95: 2509-2514, 1998; Fallaux, et al., *Hum. Gene Ther.*, 7: 215-222, 1996). Following large-scale infection of HEK293 cell cultures, the recombinant adenoviruses were purified by two consecutive CsCl ultracentrifugation steps, dialyzed, and titrated.

Adenoviral Infection of Large-Scale Cultures of Infected HTB-13 Cells and Purification of ApoE Human HTB-13 cells (SW 1783 human astrocytomas) grown to 80% confluence in Leibovitz L-15 medium containing 10% FBS were infected with adenoviruses expressing apoE4 at an moi of 20. After 24 hours of infection, cells were washed twice with serum free medium, preincubated in serum-free medium for 30 minutes, and fresh serum free medium was added. After 24 hours, the medium was harvested and fresh serum-free medium was added to the cells. The harvest was repeated 8-10 times. Yields of 50-100 mg/liter apoE were obtained. ApoE was purified from the culture medium of adenovirus-infected HTB-13 cells using Dextran-sulfate Sepharose ion exchange chromatography (Li, et al., *Biochem.* 42: 10406-10417, 2003).

Animal Studies

Female apoE-deficient (apoE$^{-/-}$) and apoExLDLr double-deficient (apoE$^{-/-}$xLDLr$^{-/-}$) mice, 4-6 weeks of age, were used (Jackson Laboratories). Groups were formed after determining the fasting cholesterol and triglyceride levels of the individual mice to ensure similar average cholesterol and triglyceride levels among groups.

For the adenovirus infections, groups of 4-6 mice were injected intravenously through the tail vein with doses of $5 \times 10^8$ or $2 \times 10^9$ pfu of the apoE4-expressing adenovirus. Blood was obtained daily following a 4 hour fasting period for up to 9 days after injection.

Figure 12:
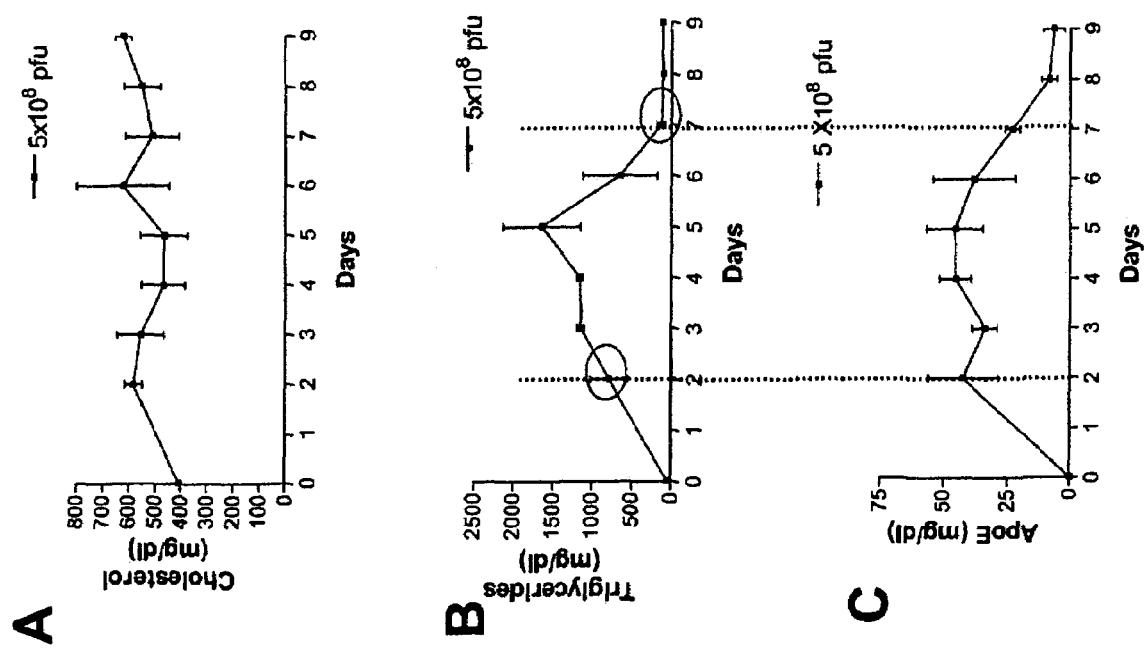
FIG. 12A-C are graphs of the time course of plasma cholesterol, triglyceride, and apoE levels, respectively, in apoE$^{-/-} \times$LDLr$^{-/-}$ mice infected with low ($5 \times 10^8$ pfu) doses of recombinant adenovirus expressing apoE4.

Gene Transfer of Low Doses of ApoE Does not Clear Cholesterol in ApoE$^{-/-}$xLDLr$^{-/-}$ Mice The plasma lipid and apoE profiles of apoE$^{-/-}$xLDLr$^{-/-}$ mice infected with low doses ($5 \times 10^8$ pfu) of the apoE-expressing adenovirus were drastically different from the lipid profiles of the apoE$^{-/-}$ mice infected with the same adenovirus dose. Plasma cholesterol levels remained high two to nine days post-infection (FIG. 12A). In addition, hypertriglyceridemia was induced when the steady-state plasma apoE levels were approximately 30 mg/dl and disappeared when the apoE levels dropped below 22 mg/dl (compare FIGS. 12B and 12C). The steady state plasma apoE levels of the apoE$^{-/-}$ micexLDLr$^{-/-}$ mice infected with low does of the apoE-expressing adenovirus were elevated 2 to 6 days post infection (FIG. 12C). The increase in the steady-state plasma apoE levels reflects defective clearance of apoE-containing triglyceride rich lipoproteins. This is in contrast to the apoE$^{-/-}$ mice infected with low doses of the apoE4-expressing adenovirus which showed very low steady-state apoE levels and efficient clearance of lipoprotein remnants (FIGS. 11A and 11C).

Bolus Infusion of ApoE Affects Differently Plasma Lipid Levels in ApoE$^{-/-}$ Mice and ApoE$^{-/-\times LDLr-/-}$ Mice The ability of apoE to clear lipoprotein remnants was assessed by bolus injection of a 10 mg/ml solution of apoE in PBS and collection of blood at different time points. Plasma samples isolated 1 minute post-infection were used as control.

Figure 13:
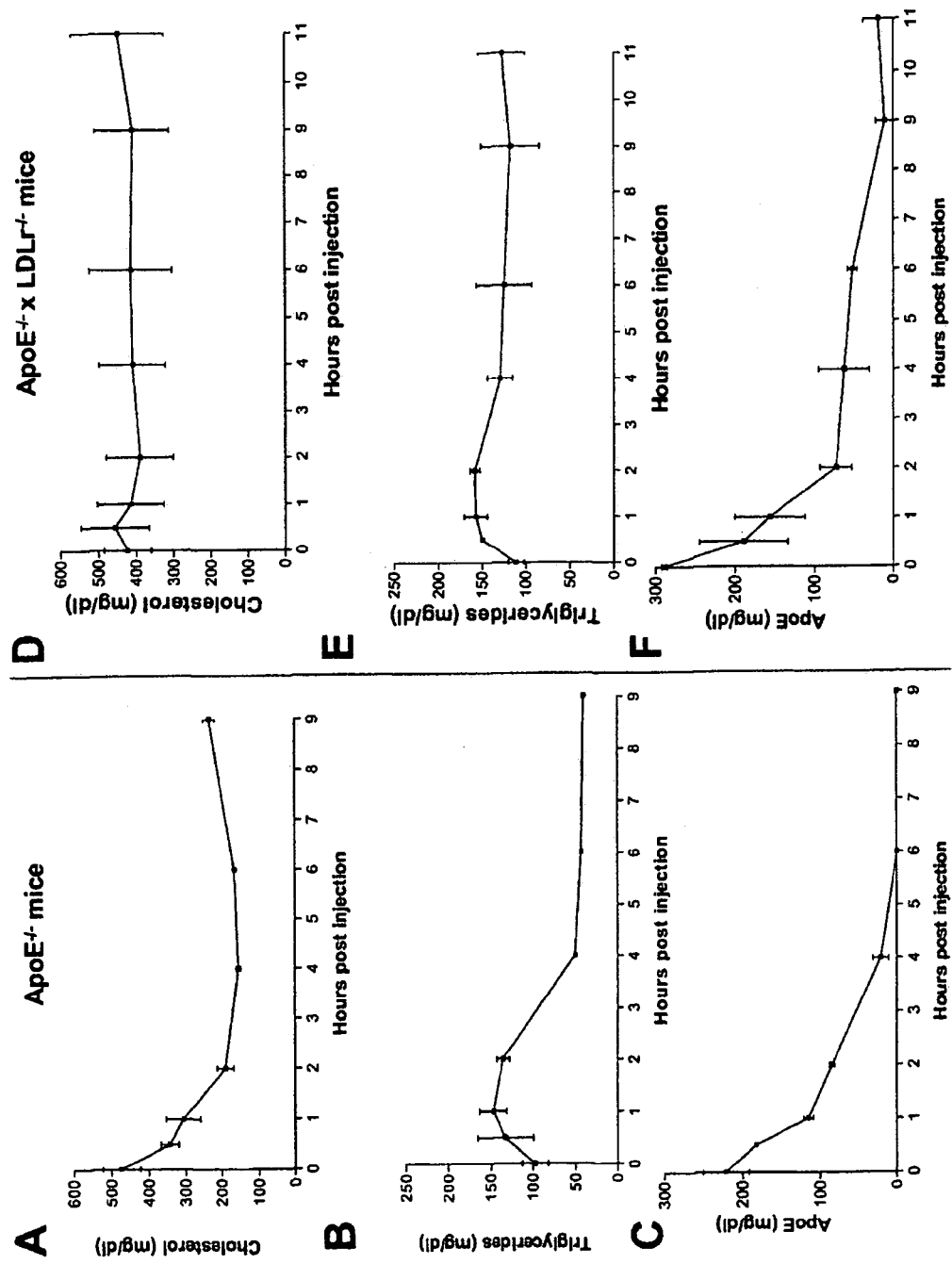
FIGS. 13A-C are graphs of the time course of plasma cholesterol, triglyceride, and apoE levels, respectively, in apoE$^{-/-}$ mice following a 10 mg/ml bolus intravenous injection of apoE4.
FIGS. 13D-F are graphs of the time course of plasma cholesterol, triglyceride, and apoE levels, respectively, in apoE$^{-/-} \times$LDLr$^{-/-}$ mice following a 10 mg/ml bolus intravenous injection of apoE4.
Figure 14:
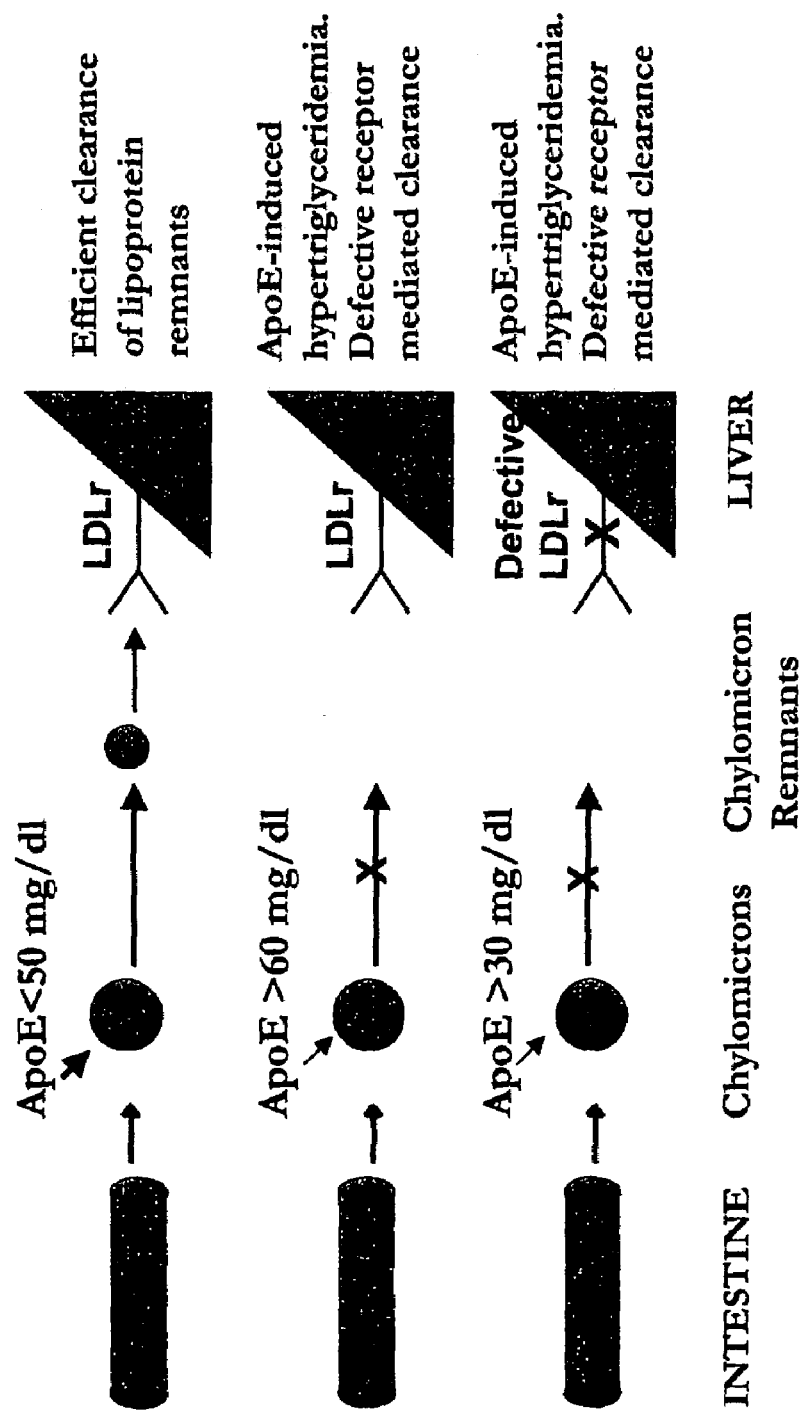
FIG. 14 is a schematic representation summarizing the contribution of apoE and LDL receptor to the clearance of apoE-containing lipoproteins and the induction of hypertriglyceridemia.

Bolus injection of apoE corrected transiently plasma cholesterol levels of the apoE$^{-/-}$ mice (FIG. 13A), but did not affect plasma cholesterol levels of the apoE$^{-/-}$xLDLr$^{-/-}$ double-deficient mice (FIG. 13D). Bolus injection of apoE also caused a transient modest increase in plasma triglycerides in both strains of mice (FIGS. 13B and 13E). Injected apoE was totally undetectable in the plasma of the apoE$^{-/-}$ mice within 6 hours post-injection (FIG. 13C); however, low levels of apoE were detected in the plasma of the apoE$^{-/-}$x LDLr$^{-/-}$ mice up to 11 hours post-injection (FIG. 13F). FIG. 14 summarized the contribution of apoE and the LDL receptor to the clearance of apoE-containing lipoproteins and the induction of hypertriglyceridemia.

ApoE, at physiological concentrations, is required for the catabolism of lipoprotein remnants via the LDL-receptor, other lipoprotein receptors, or HSPG. Low levels of apoE produced by the liver following adenovirus infection or bolus injection into the plasma can transiently clear cholesterol in apoE$^{-/-}$ mice that express the LDL receptor. However, similar treatments of double-deficient apoE$^{-/-}$x LDLr$^{-/-}$ mice did not clear cholesterol from the plasma. Thus, the predominant physiological receptor involved int eh clearance of apoE-containing lipoproteins in mice is the LDL receptor (FIG. 14).

Injection of Mice with ApoE

For the bolus injection of purified aopE4, following a 4 hour fasting, groups of 3-4 female mice with similar fasting cholesterol and triglyceride levels were injected intravenously through the tail vein with 400 µl of a 10 mg/ml solution of apoE in PBS. Blood samples (15 µl) were collected from the tail of the injected mice from 30 minutes to 11 hours post-injection. Five microliters of plasma were diluted 5-fold in PBS and analyzed for cholesterol and triglyceride levels. Plasma samples isolated 1 minute after injection of the apoE4 were used as a control.

Gene Therapy for the Treatment of Hypercholesterolemia

Therapeutic apoE proteins, administered by gene therapy, may be used for the treatment of hypercholesterolemia. Heterologous nucleic acid molecules, encoding for example, apoE4-mut1 protein can be delivered to blood stream of a mammal (e.g., a human). Expression of anti-hypercholesterolemia proteins in tissues that normally express apoE (e.g., the liver) can reduce the plasma cholesterol levels without inducing hypertriglyceridemia. The nucleic acid molecules must be delivered to those cells in a form in which they can be taken up by the cells and so that sufficient levels of the therapeutic apoE protein can be produced.

Transducing viral (e.g., retroviral, adenoviral, and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a the therapeutic apoE gene construct can be cloned into a retroviral vector and expression can be driven from its endogenous promoter, from the retroviral long terminal repeat, or from a promoter specifically expressed in a target cell type of interest (e.g., a neoplasm endothelial cell). Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346). Most preferably, a viral vector is used to administer the therapeutic apoE nucleic acid to the liver.

Non-viral approaches can also be employed for the introduction of therapeutic nucleic acids to a cell of a patient having hypercholesterolemia. For example, a nucleic acid molecule can be introduced into a cell by administering the nucleic acid in the presence of lipofection (Felgner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Preferably the nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of normal genes into the affected tissues of a patient can also be accomplished by transferring a normal nucleic acid into a cultivatable cell type ex vivo (e.g., an autologous or heterologous primary cell or progeny thereof), after which the cell (or its descendants) are injected into a targeted tissue.

cDNA expression for use in gene therapy methods can be directed from any suitable promoter (e.g., an endocan promoter, Flt-1 promoter, or other tumor endothelial promoter identified using the methods described herein), and regulated by any appropriate mammalian regulatory element. For example, if desired, an enhancers known to preferentially direct gene expression in a tumor endothelial cell, (e.g., the 300 base pair Tie-2 intronic enhancer element described herein) can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Synthesis of Therapeutic ApoE Proteins

Nucleic acids that encode a therapeutic apoE protein may be introduced into various cell types or cell-free systems for expression, thereby allowing purification of the protein for biochemical characterization, large-scale production, and patient therapy.

Eukaryotic and prokaryotic DRAGON expression systems may be generated in which a therapeutic apoE nucleic acid sequence is introduced into a plasmid or other vector, which is then used to transform living cells. Typical expression vectors contain promoters that direct the synthesis of large amounts of mRNA corresponding to the inserted therapeutic apoE nucleic acid in the plasmid-bearing cells. They may also include a eukaryotic or prokaryotic origin of replication sequence allowing for their autonomous replication within the host organism, sequences that encode genetic traits that allow vector-containing cells to be selected for in the presence of otherwise toxic drugs, and sequences that increase the efficiency with which the synthesized mRNA is translated. Stable long-term vectors may be maintained as freely replicating entities by using regulatory elements of, for example, viruses (e.g., the OriP sequences from the Epstein Barr Virus genome). Cell lines may also be produced that have integrated the vector into the genomic DNA, and in this manner the gene product is produced on a continuous basis.

Expression of foreign sequences in bacteria, such as *Escherichia coli*, requires the insertion of the therapeutic apoE nucleic acid sequence into a bacterial expression vector. Such plasmid vectors contain several elements required for the propagation of the plasmid in bacteria, and for expression of the DNA inserted into the plasmid. Propagation of only plasmid-bearing bacteria is achieved by introducing, into the plasmid, selectable marker-encoding sequences that allow plasmid-bearing bacteria to grow in the presence of otherwise toxic drugs. The plasmid also contains a transcriptional promoter capable of producing large amounts of mRNA from the cloned gene. Such promoters may be (but are not necessarily) inducible promoters that initiate transcription upon induction. The plasmid also preferably contains a polylinker to simplify insertion of the gene in the correct orientation within the vector.

Mammalian cells can also be used to express a therapeutic apoE protein. Stable or transient cell line clones can be made using therapeutic apoE expression vectors to produce therapeutic apoE proteins in a soluble (truncated and tagged) or membrane anchored (native) form. Appropriate cell lines include, for example, COS, HEK293T, CHO, or NIH cell lines.

Once the appropriate expression vectors containing a therapeutic apoE nucleic acid is constructed, it is introduced into an appropriate host cell by transformation techniques, such as, but not limited to, calcium phosphate transfection, DEAE-dextran transfection, electroporation, microinjection, protoplast fusion, or liposome-mediated transfection. The host cells that are transfected with the vectors of this invention may include (but are not limited to) *E. coli* or other bacteria, yeast, fungi, insect cells (using, for example, baculoviral vectors for expression in SF9 insect cells), or cells derived from mice, humans, or other animals. Those skilled in the art of molecular biology will understand that a wide variety of expression systems and purification systems may be used to produce recombinant therapeutic apoE proteins. Some of these systems are described, for example, in Ausubel et al. (supra).

Once a recombinant protein is expressed, it can be isolated from cell lysates using protein purification techniques such as affinity chromatography. Once isolated, the recombinant protein can, if desired, be purified further by e.g., by high performance liquid chromatography (HPLC; e.g., see Fisher, Laboratory Techniques In Biochemistry And Molecular Biology, Work and Burdon, Eds., Elsevier, 1980).

Pharmaceutical Compositions for Administering a Therapeutic ApoE Protein

The present invention includes the administration of a therapeutic apoE protein for the treatment or prevention of hypercholesterolemia. The administration of a therapeutic apoE protein, regardless of its method of manufacture, reduces plasma cholesterol levels without inducing hypertriglyceridemia.

Peptide agents of the invention, such as a therapeutic apoE protein, can be administered to a subject, e.g., a human, directly or in combination with any pharmaceutically acceptable carrier or salt known in the art. Pharmaceutically acceptable salts may include non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like. One exemplary pharmaceutically acceptable carrier is physiological saline. Other physiologically acceptable carriers and their formulations are known to one skilled in the art and described, for example, in Remington's Pharmaceutical Sciences, (19th edition), ed. A. Gennaro, 1995, Mack Publishing Company, Easton, Pa.

Pharmaceutical formulations of a therapeutically effective amount of a therapeutic apoE protein of the invention, or pharmaceutically acceptable salt-thereof, is preferably administered by intravenous injection, but can be administered orally or by other parenteral routes (e.g. intramuscular, intraperitoneal, or subcutaneous injection), in an admixture with a pharmaceutically acceptable carrier adapted for the route of administration.

Methods well known in the art for making formulations are found, for example, in Remington's Pharmaceutical Sciences (19th edition), ed. A. Gennaro, 1995, Mack Publishing Company, Easton, Pa. Compositions intended for oral use may be prepared in solid or liquid forms according to any method known to the art for the manufacture of pharmaceutical compositions. The compositions may optionally contain sweetening, flavoring, coloring, perfuming, and/or preserving agents in order to provide a more palatable preparation. Solid dosage forms for oral administration include capsules, tablets, pills, powders, and granules. In such solid forms, the active compound is admixed with at least one inert pharmaceutically acceptable carrier or excipient. These may include, for example, inert diluents, such as calcium carbonate, sodium carbonate, lactose, sucrose, starch, calcium phosphate, sodium phosphate, or kaolin. Binding agents, buffering agents, and/or lubricating agents (e.g., magnesium stearate) may also be used. Tablets and pills can additionally be prepared with enteric coatings.

Liquid dosage forms for oral administration include pharmaceutically acceptable emulsions, solutions, suspensions, syrups, and soft gelatin capsules. These forms contain inert diluents commonly used in the art, such as water or an oil medium. Besides such inert diluents, compositions can also include adjuvants, such as wetting agents, emulsifying agents, and suspending agents.

Formulations for parenteral administration include sterile aqueous or non-aqueous solutions, suspensions, or emulsions. Examples of suitable vehicles include propylene glycol, polyethylene glycol, vegetable oils, gelatin, hydrogenated naphalenes, and injectable organic esters, such as ethyl oleate. Such formulations may also contain adjuvants, such as preserving, wetting, emulsifying, and dispersing agents. Biocompatible, biodegradable lactide polymer, lactide/glycolide copolymer, or polyoxyethylene-polyoxypropylene copolymers may be used to control the release of the compounds. Other potentially useful parenteral delivery systems for the proteins of the invention include ethylene-vinyl acetate copolymer particles, osmotic pumps, implantable infusion systems, and liposomes.

Liquid formulations can be sterilized by, for example, filtration through a bacteria-retaining filter, by incorporating sterilizing agents into the compositions, or by irradiating or heating the compositions. Alternatively, they can also be manufactured in the form of sterile, solid compositions which can be dissolved in sterile water or some other sterile injectable medium immediately before use.

The amount of active ingredient in the compositions of the invention can be varied. One skilled in the art will appreciate that the exact individual dosages may be adjusted somewhat depending upon a variety of factors, including the protein being administered, the time of administration, the route of administration, the nature of the formulation, the rate of excretion, the nature of the subject's conditions, and the age, weight, health, and gender of the patient. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise therapeutically effective dosage will be determined by the attending physician in consideration of the above identified factors.

The protein or therapeutic compound of the invention can be administered in a sustained release composition, such as those described in, for example, U.S. Pat. No. 5,672,659 and U.S. Pat. No. 5,595,760. The use of immediate or sustained release compositions depends on the type of condition being treated. If the condition consists of an acute or subacute disorder, a treatment with an immediate release form will be preferred over a prolonged release composition. Alternatively, for preventative or long-term treatments, a sustained released composition will generally be preferred.

OTHER EMBODIMENTS

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for reducing plasma cholesterol in a mammal, without inducing hypertriglyceridemia, said method comprising administering to said mammal a therapeutic apoE protein comprising a sequence having at least 95% sequence identity to SEQ ID NO: 1 and at least one amino acid substitution in the carboxy-terminal region.

2. The method of claim 1, wherein said mammal is a human.

3. The method of claim 1, wherein said therapeutic apoE protein comprises at least one amino acid substitution selected from the group consisting of L261X, W264X, F265X, L268X, and V269X, wherein X is any amino acid.

4. The method of claim 3, wherein X is alanine.

5. The method of claim 1, wherein said therapeutic apoE protein comprises at least one amino acid substitution selected from the group consisting of L261A, W264A, F265A, L268A, and V269A.

6. The method of claim 5, wherein said therapeutic apoE protein comprises the amino acid substitutions L261A, W264A, F265A, L268A, and V269A.

7. The method of claim 1, wherein said therapeutic apoE protein is apoE4.

8. The method of claim 1, wherein said therapeutic apoE protein comprises at least one amino acid substitution selected from the group consisting of W276X, L279X, V283X, V287X, and V293X, wherein X is any amino acid.

9. The method of claim 8, wherein X is alanine.

10. The method of claim 1, wherein said therapeutic apoE protein comprises at least one amino acid substitution selected from the group consisting of W276A, L279A, V283A, V287A, and V293A.

11. The method of claim 10, wherein said therapeutic apoE protein comprises the amino acid substitutions W276A, L279A, V283A, V287A, and V293A.

12. The method of claim 1, wherein said therapeutic apoE protein is apoE4.

13. The method of claim 1, wherein said therapeutic apoE protein is administered by intravenous injection.

14. A therapeutic apoE protein comprising a sequence having at least 95% sequence identity to SEQ ID NO: 1 and at least one amino acid substitution in the carboxy-terminal region, wherein said protein when administered to a mammal is capable of lowering the total serum cholesterol levels without inducing hypertriglyceridemia.

15. The therapeutic apoE protein of claim 14, wherein said therapeutic apoE protein comprises at least one amino acid substitution selected from the group consisting of L261X, W264X, F265X, L268X, and V269X, wherein X is any amino acid.

16. The therapeutic apoE protein of claim 15, wherein X is alanine.

17. The therapeutic apoE protein of claim 14, wherein said therapeutic apoE protein comprises at least one amino acid substitution selected from the group consisting of L261A, W264A, F265A, L268A, and V269A.

18. The therapeutic apoE protein of claim 17, wherein said therapeutic apoE protein comprises the amino acid substitutions L261A, W264A, F265A, L268A, and V269A.

19. The therapeutic apoE protein of claim 14, wherein said therapeutic apoE protein is apoE4.

20. The therapeutic apoE protein of claim 14, wherein said therapeutic apoE protein comprises at least one amino acid substitution selected from the group consisting of W276X, L279X, V283X, V287X, and V293X, wherein X is any amino acid.

21. The therapeutic apoE protein of claim 20, wherein X is alanine.

22. The therapeutic apoE protein of claim 1, wherein said therapeutic apoE protein comprises at least one amino acid substitution selected from the group consisting of W276A, L279A, V283A, V287A, and V293A.

23. The therapeutic apoE protein of claim 22, wherein said therapeutic apoE protein comprises the amino acid substitutions W276A, L279A, V283A, V287A, and V293A.

24. The therapeutic apoE protein of claim 14, wherein said therapeutic apoE protein is apoE4.

25. The therapeutic apoE protein of claim 17, wherein said therapeutic apoE protein comprises the amino acid substitutions L261A, W264A, and F265A.

* * * * *

UNITED STATES PATENT AND TRADEMARK OFFICE
CERTIFICATE OF CORRECTION

PATENT NO. : 7,309,606 B2
APPLICATION NO. : 11/220485
DATED : December 18, 2007
INVENTOR(S) : Vassilis I. Zannis and Kyriakos E. Kypreos It is certified that error appears in the above-identified patent and that said Letters Patent is hereby corrected as shown below:

Title Page (75) Inventors: should read as follows:

Vassilis I. Zannis, Newton, MA (US);
Kyriakos E. Kypreos, Ialyssos-Rhodes (GR)

Signed and Sealed this

Twenty-seventh Day of May, 2008

JON W. DUDAS
*Director of the United States Patent and Trademark Office*

SEQUENCE LISTING

```
<160> NUMBER OF SEQ ID NOS: 6

<210> SEQ ID NO 1
<211> LENGTH: 299
<212> TYPE: PRT
<213> ORGANISM: Homo sapiens

<400> SEQUENCE: 1

Lys Val Glu Gln Ala Val Glu Thr Glu Pro Glu Pro Glu Leu Arg Gln
 1               5                  10                  15

Gln Thr Glu Trp Gln Ser Gly Gln Arg Trp Glu Leu Ala Leu Gly Arg
            20                  25                  30

Phe Trp Asp Tyr Leu Arg Trp Val Gln Thr Leu Ser Glu Gln Val Gln
        35                  40                  45
```

-continued

```
Glu Glu Leu Leu Ser Ser Gln Val Thr Gln Glu Leu Arg Ala Leu Met
     50                  55                  60

Asp Glu Thr Met Lys Glu Leu Lys Ala Tyr Lys Ser Glu Leu Glu Glu
 65                  70                  75                  80

Gln Leu Thr Pro Val Ala Glu Glu Thr Arg Ala Arg Leu Ser Lys Glu
                     85                  90                  95

Leu Gln Ala Ala Gln Ala Arg Leu Gly Ala Asp Met Glu Asp Val Arg
                100                 105                 110

Gly Arg Leu Val Gln Tyr Arg Gly Glu Val Gln Ala Met Leu Gly Gln
            115                 120                 125

Ser Thr Glu Glu Leu Arg Val Arg Leu Ala Ser His Leu Arg Lys Leu
    130                 135                 140

Arg Lys Arg Leu Leu Arg Asp Ala Asp Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
                180                 185                 190

Ala Thr Val Gly Ser Leu Ala Gly Gln Pro Leu Gln Glu Arg Ala Gln
            195                 200                 205

Ala Trp Gly Glu Arg Leu Arg Ala Arg Met Glu Glu Met Gly Ser Arg
    210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
                260                 265                 270

Gln Arg Gln Trp Ala Gly Leu Val Glu Lys Val Gln Ala Ala Val Gly
            275                 280                 285

Thr Ser Ala Ala Pro Val Pro Ser Asp Asn His
    290                 295

<210> SEQ ID NO 2
<211> LENGTH: 299
<212> TYPE: PRT
<213> ORGANISM: Homo sapiens

<400> SEQUENCE: 2

Lys Val Glu Gln Ala Val Glu Thr Glu Pro Glu Pro Glu Leu Arg Gln
  1               5                  10                  15

Gln Thr Glu Trp Gln Ser Gly Gln Arg Trp Glu Leu Ala Leu Gly Arg
                 20                  25                  30

Phe Trp Asp Tyr Leu Arg Trp Val Gln Thr Leu Ser Glu Gln Val Gln
             35                  40                  45

Glu Glu Leu Leu Ser Ser Gln Val Thr Gln Glu Leu Arg Ala Leu Met
     50                  55                  60

Asp Glu Thr Met Lys Glu Leu Lys Ala Tyr Lys Ser Glu Leu Glu Glu
 65                  70                  75                  80

Gln Leu Thr Pro Val Ala Glu Glu Thr Arg Ala Arg Leu Ser Lys Glu
                     85                  90                  95

Leu Gln Ala Ala Gln Ala Arg Leu Gly Ala Asp Met Glu Asp Val Cys
                100                 105                 110

Gly Arg Leu Val Gln Tyr Arg Gly Glu Val Gln Ala Met Leu Gly Gln
            115                 120                 125
```

```
Ser Thr Glu Glu Leu Arg Val Arg Leu Ala Ser His Leu Arg Lys Leu
130                 135                 140

Arg Lys Arg Leu Leu Arg Asp Ala Asp Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
            180                 185                 190

Ala Thr Val Gly Ser Leu Ala Gly Gln Pro Leu Gln Glu Arg Ala Gln
            195                 200                 205

Ala Trp Gly Glu Arg Leu Arg Ala Arg Met Glu Glu Met Gly Ser Arg
210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
            260                 265                 270

Gln Arg Gln Trp Ala Gly Leu Val Glu Lys Val Gln Ala Ala Val Gly
            275                 280                 285

Thr Ser Ala Ala Pro Val Pro Ser Asp Asn His
290                 295

<210> SEQ ID NO 3
<211> LENGTH: 299
<212> TYPE: PRT
<213> ORGANISM: Homo sapiens

<400> SEQUENCE: 3

Lys Val Glu Gln Ala Val Glu Thr Glu Pro Glu Pro Glu Leu Arg Gln
1               5                   10                  15

Gln Thr Glu Trp Gln Ser Gly Gln Arg Trp Glu Leu Ala Leu Gly Arg
            20                  25                  30

Phe Trp Asp Tyr Leu Arg Trp Val Gln Thr Leu Ser Glu Gln Val Gln
        35                  40                  45

Glu Glu Leu Leu Ser Ser Gln Val Thr Gln Glu Leu Arg Ala Leu Met
50                  55                  60

Asp Glu Thr Met Lys Glu Leu Lys Ala Tyr Lys Ser Glu Leu Glu Glu
65                  70                  75                  80

Gln Leu Thr Pro Val Ala Glu Glu Thr Arg Ala Arg Leu Ser Lys Glu
                85                  90                  95

Leu Gln Ala Ala Gln Ala Arg Leu Gly Ala Asp Met Glu Asp Val Cys
            100                 105                 110

Gly Arg Leu Val Gln Tyr Arg Gly Glu Val Gln Ala Met Leu Gly Gln
        115                 120                 125

Ser Thr Glu Glu Leu Arg Val Arg Leu Ala Ser His Leu Arg Lys Leu
130                 135                 140

Arg Lys Arg Leu Leu Arg Asp Ala Asp Asp Leu Gln Lys Cys Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
            180                 185                 190

Ala Thr Val Gly Ser Leu Ala Gly Gln Pro Leu Gln Glu Arg Ala Gln
            195                 200                 205
```

```
Ala Trp Gly Glu Arg Leu Arg Ala Arg Met Glu Met Gly Ser Arg
    210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
                260                 265                 270

Gln Arg Gln Trp Ala Gly Leu Val Glu Lys Val Gln Ala Ala Val Gly
                275                 280                 285

Thr Ser Ala Ala Pro Val Pro Ser Asp Asn His
    290                 295

<210> SEQ ID NO 4
<211> LENGTH: 299
<212> TYPE: PRT
<213> ORGANISM: Homo sapiens

<400> SEQUENCE: 4

Lys Val Glu Gln Ala Val Glu Thr Glu Pro Glu Pro Glu Leu Arg Gln
1               5                   10                  15

Gln Thr Glu Trp Gln Ser Gly Gln Arg Trp Glu Leu Ala Leu Gly Arg
                20                  25                  30

Phe Trp Asp Tyr Leu Arg Trp Val Gln Thr Leu Ser Glu Gln Val Gln
            35                  40                  45

Glu Glu Leu Leu Ser Ser Gln Val Thr Gln Glu Leu Arg Ala Leu Met
50                  55                  60

Asp Glu Thr Met Lys Glu Leu Lys Ala Tyr Lys Ser Glu Leu Glu Glu
65                  70                  75                  80

Gln Leu Thr Pro Val Ala Glu Glu Thr Arg Ala Arg Leu Ser Lys Glu
                85                  90                  95

Leu Gln Ala Ala Gln Ala Arg Leu Gly Ala Asp Met Glu Asp Val Cys
                100                 105                 110

Gly Arg Leu Val Gln Tyr Arg Gly Glu Val Gln Ala Met Leu Asp Gln
            115                 120                 125

Ser Thr Glu Glu Leu Arg Val Arg Leu Ala Ser His Leu Arg Lys Leu
130                 135                 140

Arg Lys Arg Leu Leu Arg Asp Ala Asp Asp Leu Gln Lys Cys Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
                180                 185                 190

Ala Thr Val Gly Ser Leu Ala Gly Gln Pro Leu Gln Glu Arg Ala Gln
            195                 200                 205

Ala Trp Gly Glu Arg Leu Arg Ala Arg Met Glu Met Gly Ser Arg
    210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
                260                 265                 270
```

```
Gln Arg Gln Trp Ala Gly Leu Val Glu Lys Val Gln Ala Ala Val Gly
        275                 280                 285

Thr Ser Ala Ala Pro Val Pro Ser Asp Asn His
    290                 295

<210> SEQ ID NO 5
<211> LENGTH: 299
<212> TYPE: PRT
<213> ORGANISM: Homo sapiens

<400> SEQUENCE: 5

Lys Val Glu Gln Ala Val Glu Thr Glu Pro Glu Pro Glu Leu Arg Gln
  1               5                  10                  15

Gln Thr Glu Trp Gln Ser Gly Gln Arg Trp Glu Leu Ala Leu Gly Arg
         20                  25                  30

Phe Trp Asp Tyr Leu Arg Trp Val Gln Thr Leu Ser Glu Gln Val Gln
         35                  40                  45

Glu Glu Leu Leu Ser Ser Gln Val Thr Gln Glu Leu Arg Ala Leu Met
 50                  55                  60

Asp Glu Thr Met Lys Glu Leu Lys Ala Tyr Lys Ser Glu Leu Glu Glu
 65                  70                  75                  80

Gln Leu Thr Pro Val Ala Glu Glu Thr Arg Ala Arg Leu Ser Lys Glu
                 85                  90                  95

Leu Gln Ala Ala Gln Ala Arg Leu Gly Ala Asp Met Glu Asp Val Cys
            100                 105                 110

Gly Arg Leu Val Gln Tyr Arg Gly Glu Val Gln Ala Met Leu Gly Gln
        115                 120                 125

Ser Thr Glu Glu Leu Arg Val Arg Leu Ala Ser His Leu Arg Lys Leu
    130                 135                 140

Cys Lys Arg Leu Leu Arg Asp Ala Asp Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
            180                 185                 190

Ala Thr Val Gly Ser Leu Ala Gly Gln Pro Leu Gln Glu Arg Ala Gln
        195                 200                 205

Ala Trp Gly Glu Arg Leu Arg Ala Arg Met Glu Glu Met Gly Ser Arg
    210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
            260                 265                 270

Gln Arg Gln Trp Ala Gly Leu Val Glu Lys Val Gln Ala Ala Val Gly
        275                 280                 285

Thr Ser Ala Ala Pro Val Pro Ser Asp Asn His
    290                 295

<210> SEQ ID NO 6
<211> LENGTH: 299
<212> TYPE: PRT
<213> ORGANISM: Homo sapiens
```

```
<400> SEQUENCE: 6

Lys Val Glu Gln Ala Val Glu Thr Glu Pro Glu Pro Glu Leu Arg Gln
  1               5                  10                  15

Gln Thr Glu Trp Gln Ser Gly Gln Arg Trp Glu Leu Ala Leu Gly Arg
                 20                  25                  30

Phe Trp Asp Tyr Leu Arg Trp Val Gln Thr Leu Ser Glu Gln Val Gln
             35                  40                  45

Glu Glu Leu Leu Ser Ser Gln Val Thr Gln Glu Leu Arg Ala Leu Met
         50                  55                  60

Asp Glu Thr Met Lys Glu Leu Lys Ala Tyr Lys Ser Glu Leu Glu Glu
 65                  70                  75                  80

Gln Leu Thr Pro Val Ala Glu Glu Thr Arg Ala Arg Leu Ser Lys Glu
                 85                  90                  95

Leu Gln Ala Ala Gln Ala Arg Leu Gly Ala Asp Met Glu Asp Val Cys
                100                 105                 110

Gly Arg Leu Val Gln Tyr Arg Gly Glu Val Gln Ala Met Leu Gly Gln
                115                 120                 125

Ser Thr Glu Glu Leu Arg Val Arg Leu Ala Ser His Leu Arg Lys Leu
130                 135                 140

Arg Gln Arg Leu Leu Arg Asp Ala Asp Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
                180                 185                 190

Ala Thr Val Gly Ser Leu Ala Gly Gln Pro Leu Gln Glu Arg Ala Gln
                195                 200                 205

Ala Trp Gly Glu Arg Leu Arg Ala Arg Met Glu Glu Met Gly Ser Arg
                210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
                260                 265                 270

Gln Arg Gln Trp Ala Gly Leu Val Glu Lys Val Gln Ala Ala Val Gly
                275                 280                 285

Thr Ser Ala Ala Pro Val Pro Ser Asp Asn His
290                 295
```